United States Patent
Wood et al.

(10) Patent No.: US 7,038,043 B1
(45) Date of Patent: May 2, 2006

(54) GLYCOSYLATED INDOLOCARBAZOLE SYNTHESIS

(75) Inventors: John L. Wood, North Haven, CT (US); Brian M. Stoltz, Auburn, CA (US); Hans-Jurgen Dietrich, Zurich (CH); Derek A. Pflum, Northville, MI (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/482,235

(22) Filed: Jan. 13, 2000

Related U.S. Application Data

(60) Division of application No. 09/206,082, filed on Dec. 4, 1998, now Pat. No. 6,037,468, which is a continuation-in-part of application No. 08/817,230, filed as application No. PCT/IB96/00987 on Aug. 9, 1996, now abandoned.

(60) Provisional application No. 60/002,164, filed on Aug. 11, 1995.

(51) Int. Cl.
C07D 273/00 (2006.01)

(52) U.S. Cl. ..................................................... 540/545
(58) Field of Classification Search ................. 540/545
See application file for complete search history.

(56) References Cited

FOREIGN PATENT DOCUMENTS

JP          05-247054          9/1993

OTHER PUBLICATIONS

Frendhagen, A., & Peter, H.H., Tetrahedron 52:1235-1238 (1996).

(Continued)

*Primary Examiner*—Brenda Coleman
(74) *Attorney, Agent, or Firm*—Carmody & Torrance LLP

(57) ABSTRACT

Indolocarbazoles are furanosylated (e.g., 7) with acetals (e.g., 8) or their open chain congeners (e.g., 9) under conditions known to promote acetal exchange or formation, such as protic or Lewis acids. Furanosylated indolocarbazoles (e.g., 10) are also prepared via ring contraction of pyranosylated indolocarbazoles (e.g., 11) under conditions know to effect oxidation and benzylic acid type rearrangements, and pyranosylated indolocarbazoles (e.g., 11) are prepared via ring expansion of the furanosylated congeners (e.g., 10)

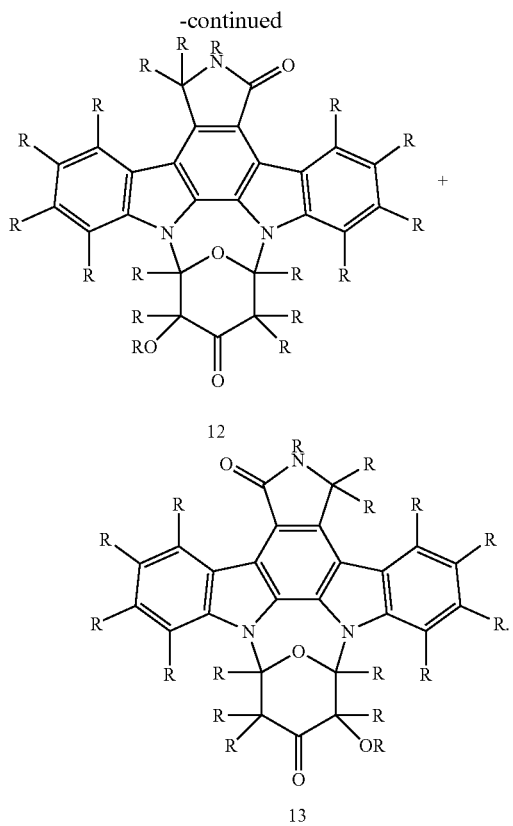

14 Claims, No Drawings

OTHER PUBLICATIONS

Link, J.T., et al., J. Am. Chem. Soc. 115:3782-3783 (1993).
Omura, S., et al., J. Antibiotics 48:535-548 (1995).

McCombie, S.W., et al., Bioorg. Med. Chem. Lett. 3:1537-1542 (1993).

Pirrung, M.C., et al., J. Org. Chem. 60:2112-2124 (1995).
Stoltz, B.M., & Wood, J.L., Tetrahedron Lett. 36:8543 (No. 47, Nov. 20, 1995).

Stoltz, B.M., & Wood, J.L., Tetrahedrom Lett. 37:3929-3930 (No. 23, Jun. 3, 1996).

Wood, J.L., et al., J. Amer. Chem. Soc. 117:10413-10414 (1995).

Wood, J.L., et al., J. Amer. Chem. Soc. 118:10656-10657 and. Supplementary Materials (No. 43, Oct. 30, 1996).

Wood, J.L., et al., Tetrahedron Lett. 37:7335-7337 and Supplementary Materials (No. 41, Oct. 7, 1996).

GLYCOSYLATED INDOLOCARBAZOLE SYNTHESIS

RELATED APPLICATION DATA

This application is a divisional of U.S. Ser. No. 09/206,082, now U.S. Pat. No. 6,037,468 filed Dec. 4, 1998, which is a continuation-in-part of U.S. application Ser. No. 08/817,230, now abandoned filed Jun. 4, 1997 and U.S. national phase entry under 35 U.S.C. 371 of PCT/IB96/00987, which had an international filing date of Aug. 9, 1996, claiming benefit of U.S. application Ser. No. 60/002,164 filed Aug. 11, 1995, all of which are incorporated herein in their entireties by reference.

TECHNICAL FIELD OF THE INVENTION

This invention relates to the synthesis of tertiary alcohols by coupling of diazo carbonyl compounds with allylic alcohols under conditions that produce carbene or carbenoid intermediates. Both furanosylated and pyranosylated indolocarbazoles are prepared, including naturally occurring compounds as well as a range of structurally diverse analogues.

BACKGROUND OF THE INVENTION

Originally discovered in the course of screening for microbial alkaloids, staurosporine and structurally related compounds have been the object of considerable investigation for various biomedical purposes for the past twenty years (for a review, see Omura, et al.). It has been recently reported that staurosporine and its derivatives, for example, inhibit smooth muscle contraction, platelet aggregation, neurotrophic activity, and, most importantly, protein kinases in vitro and in vivo (ibid).

Disruption of cellular signal transduction via kinase malfunction has been related to the onset of several disease states, including rhematoid arthritis, systemic lupus erythematosis, diabetes metillus and Alzheimer's disease. For example, the clinical severity of Alzheimer's disease correlates well with the formation of amyloid plaques and neurofibrillary tangles; both manifest paired helical filaments (PHF) that posses an overphosphorylated microtubule associated protein (M.A.P., also known as τ-protein). It has been suggested that overphosphorylation may lead to conformation changes that inhibit τ binding to microtubules. Recently, a bovine τ-kinase denominate PK40 (molecular weight 40,000) has been isolated and shown to induce a gel mobility shift of PHF-τ. PK40 is not closely associated with the cytoskeleton and appears to be a member of the extracellular regulated kinases. Specific inhibition of enzymes like PK40 by small, orally bioavailable compounds, promise to be a highly successful means of treating Alzheimer's disease.

Unfortunately, the structural homology shared by the many kinase isozymes has impeded the development of selective and therapeutically useful inhibitors. It would be desirable to have others.

SUMMARY OF THE INVENTION

It is a specific objective of the invention to provide a synthesis for (+)- and (−)- K252a, analogues of K252a, staurosporine and its congeners, (+)-RK286c and (−)-RK286c, (+)-MLR52 and (−)-MLR52, (+)-TAN 1030a, and (−)-TAN 1030a, (+)-UNC-01 and (−)-UNC-01, (+)-RK1409 and (−)-RK1409, and the like.

It is another and more general object of the invention to provide for the synthesis of furanosylated and pyranosylated indolocarbzoles, particularly the interconversion of furanosylated indolocarbazoles to the corresponding pyranosylated derivatives.

It is a further objective of the invention to provide an efficient approach to the synthesis of enantioenriched tertiary alcohols.

These and other objectives are accomplished by the present invention, which provides a process for the preparation of tertiary alcohols containing the structural features illustrated in 3 or 4 below (Scheme I). The process utilizes at least one carbonyl compound, e.g., 1 in Scheme I) and at least one allylic alcohol (e.g., 2 in Scheme I) in a coupling reaction that is run under conditions that produce carbene or carbenoid intermediates from the diazo-containing substrate. These conditions include transition metal catalysis or either thermal or photochemical decomposition. In some preferred embodiments illustrated hereafter, $Rh_2(OAc)_4$ is employed to catalyze the coupling reaction.

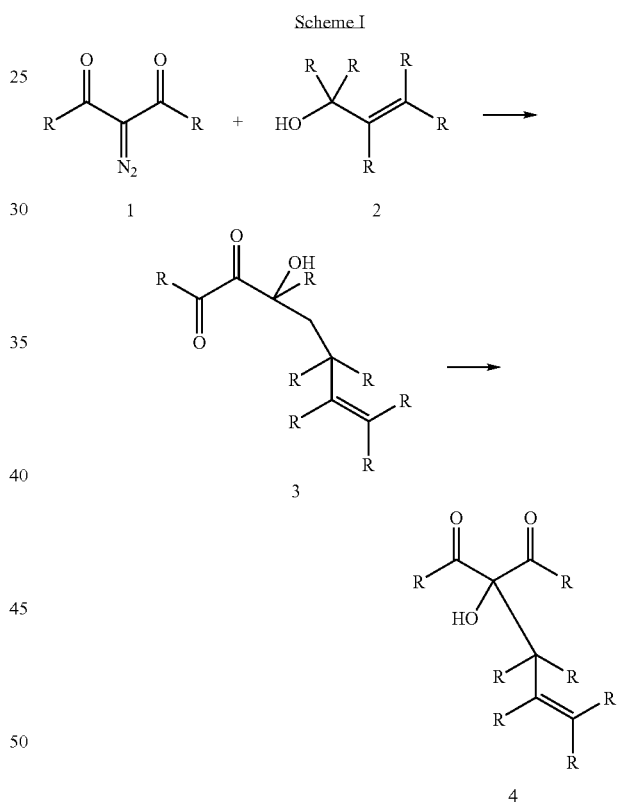

Wherein R represents a substituent comprised of any number and combination of the elements H, C, N, S, Si, O, Cl, Br, I, and F As used herein, terminology referring to R as representing a substituent comprised of any number and combination of the elements H, C, N, S, Si, O, Cl, Br, I and F refers, as is known to those skilled in the art, to alkyl, alkenyl, alkynyl, aryl, cyclic or heterocyclic substituents comprised of these elements that may be alkaloid substituents. The definition encompasses the following R groups:

a) a $C_{3-10}$ branched or unbranched alkyl, alkenyl, or alkynyl, which may be partially or fully silylated or halogenated, or combinations thereof, and optionally substituted by one to three substituents consisting of aryl or heteroaryl, wherein the aryl or heteroaryl rings may be optionally substituted with one to five groups consisting of either $C_{1-6}$ branched or unbranched alkyl, which may be partially or fully halogenated, $C_{3-8}$ cycloalkyl, halo, hydroxy, cyano, $C_{1-3}$ alkyloxy, which may be partially or fully halogenated, nitro, amino, alkylamino, dialkylamino, carbonylamine, carbonyldialkylamine, carboxy carbonyloxy $C_{1-4}$ branched or unbranched alkyl;

b) a $C_{3-10}$ branched or unbranched cycloalkyl which may be partially or fully silylated or halogenated, or combinations thereof, and optionally substituted by one to three substituents consisting of aryl or heteroaryl, wherein the aryl or heteroaryl rings may be optionally substituted with one to five groups consisting of either $C_{1-6}$ branched or unbranched alkyl, which may be partially or fully halogenated, $C_{3-8}$ cycloalkyl, halo, hydroxy, cyano, $C_{1-3}$ alkyloxy, which may be partially or fully halogenated, nitro, amino, alkylamino, dialkylamino, carbonylamine, cabonyldialkylamine, carboxy, carbonyloxy $C_{1-4}$ branched or unbranched alkyl;

c) a $C_{5-8}$ branched or unbranched cycloakenyl which may be partially or fully silylated or halogenated, or combinations thereof, and optionally substituted by one to three substituents consisting of aryl or heteroaryl, wherein the aryl or heteroaryl rings may be optionally substituted with one to five groups consisting of either $C_{1-6}$ branched or unbranched alkyl, which may be partially or fully halogenated, $C_{3-8}$ cycloalkyl, halo, hydroxy, cyano, $C_{1-3}$ alkyloxy, which may be partially or fully halogenated, nitro, amino, alkylamino, dialkylamino, carbonylamine, carbonyldialkylamine, carboxy, carbonyloxy $C_{1-4}$ branched or unbranched alkyl;

d) an aryl or heteroaryl optionally substituted with one to five groups consisting of either aryl, heteroaryl, $C_{1-6}$ branched or unbranched alkyl, which may be partially or fully silylated or halogenated, $C_{3-8}$ cycloalkyl, $C_{1-5}$ alkylaryl, halo, hydroxy, cyano, $C_{1-3}$ alkoxy, which may be partially or fully halogenated, aryloxy, heteroaryloxy, nitro, amino, alkylamino, dialkylamino, arylamino, heterarylamino, carbonylamine carbonyldialkylamine, carboxy, carbonyloxy, $C_{1-4}$ branched or unbranched alkyl, $C_{1-5}$ alkylcarbonyl $C_{1-4}$ branched or unbranched alkyl, $C_{1-5}$ alkyl or alkenylcarboxy, $C_{1-5}$ alkylamine, $C_{1-5}$ alkyldialkylamine, $C_{1-5}$ alkylthio, $C_{1-5}$ alkylsulfinyl, $C_{1-5}$ alkylsulfonyl, sulfonylamine, sulfonyldailkylamine;

(e) carboxy, carbonyloxy $C_{1-4}$ branched or unbranched alkyl, $C_{1-5}$ alkylcarbonyl $C_{1-4}$ branched or unbranched alkyl, $C_{1-5}$ alkyl or alkenylcarboxy, aryloxy, heteroaryloxy, nitro, amino, alkylamino, dialkylamino, arylamino, heteroarylamino, carbonylamine, carbonyldialkylamine$C_{1-5}$ alkylamine, $C_{1-5}$ alkyldialkylamine, $C_{1-5}$ alkylthio, $C_{1-5}$ alkylsulfinyl, $C_{1-5}$ alkylsulfonyl, sulfonylamine, sulfonyldialkylamine, and partially and fully halogenated or silylated derivatives thereof;

(f) a hydrogen;

(g) a halogen;

(h) a silyl group; and (i) mixtures of any of these.

Embodiments wherein R is H, an alkyl or an aryl are particularly preferred. In many embodiments, the R is an H or a lower unsubstituted alkyl group. As used herein, indicated above, and illustrated below, when discussing substituent R groups, the "or" indicates R groups comprising H, alkyl, or aryl groups, or mixtures of any of these. For example, the latter-mentioned subgroup encompasses alkaloids bearing only H, only alkyl groups, and mixtures thereof. Illustrative R groups in the examples that follow are H, Me, t-Bu, 3,4-DMB, and PMB.

The invention more specifically provides a process for the construction of indolocarbazoles (e.g., 7 below) from the coupling of diazo carbonyl compounds (e.g., 5) and biindoles (e.g., 6). The invention also provides a process for the stereoselective preparation of glycosylated indolocarbazoles like but not limited to 10 and 11 via furanosylation of indolocarbozoles (e.g., 7) with acetals (e.g., 8) or their open chain congeners (e.g., 9) under conditions known to promote acetal exchange or formation, such as protic or Lewis acids.

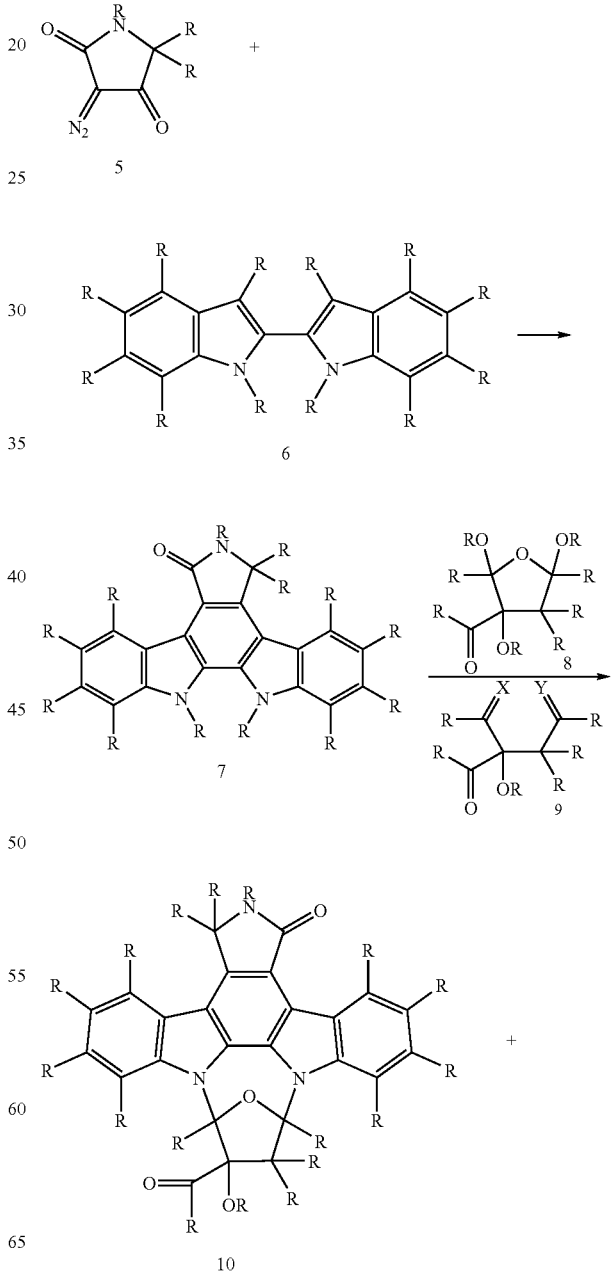

Scheme II

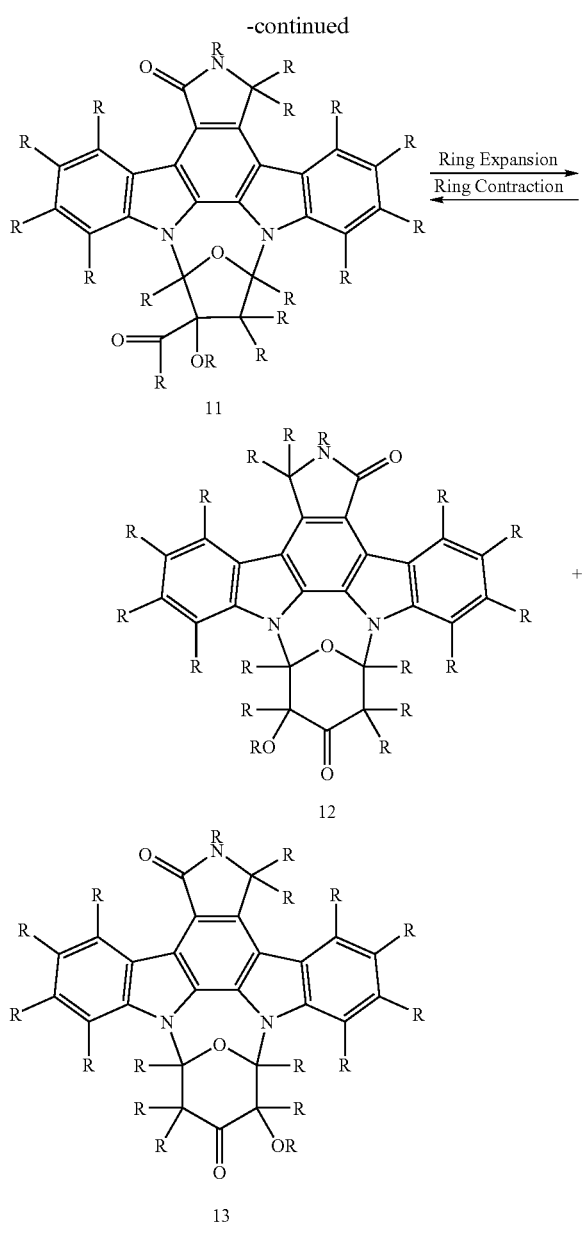

As illustrated in Scheme II above, processes of the invention also provide furanosylated indolocarbazoles (e.g., 10) via ring contraction of pyranosylated indolocarbazoles (e.g., 12) under conditions known to effect oxidation and benzylic acid type rearrangements. The invention correspondingly provides processes for the construction of pyranosylated indolocarbazoles (e.g., 12) via ring expansion of the furanosylated congeners (e.g., 10).

DETAILED DESCRIPTION OF THE INVENTION

This invention is based upon several new processes that when combined in-total or in-part can lead to the enantioselective syntheses of various indolocarbazoles.

Unless expressly noted to the contrary, the following definitions apply:

The term "alkyl" refers to a saturated aliphatic radical containing from one to ten carbon atoms. "Alkyl" refers to both branched and unbranched alkyl groups. Preferred alkyl groups are straight-chain alkyl groups containing from one to eight carbon atoms and branched alkyl groups containing from three to eight carbon atoms. More preferably alkyl groups are straight chain alkyl groups containing from one to six carbon atoms and branched alkyl groups containing from three to six carbon atoms. "Alkyl", as used herein, includes unsubstituted alkyl radicals, those radicals that are partially or fully halogenated and those radicals substituted with one to four, preferably one or two, substituents selected from amino, cyano, nitro, methoxy, ethoxy and hydroxy. The term "cycloalkyl" refers to the cyclic analog of an alkyl group, as defined above. Preferred cycloalkyl groups are saturated cycloalkyl groups containing from three to eight carbon atoms, and more preferably, three to six carbon atoms. "Alkyl" and "cycloalkyl", as used herein, include unsubstituted alkyl and cycloalkyl radicals, those radicals that are partially or fully halogenated and those radicals substituted with one to four, preferably one or two, substituents selected from halo, amino, cyano, nitro, methoxy, ethoxy and hydroxy. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom.

The terms "alkenyl" and "alkynyl" refer to mono- or polyunsaturated aliphatic hydrocarbon radical containing from two to twelve carbon atoms, containing at least one double or triple bond, respectively. "Alkenyl" and "alkynyl" refer to both branched and unbranched alkenyl and alkynyl groups. Preferred alkenyl and alkynyl groups are straight chain alkenyl or alkynyl groups containing from two to eight carbon atoms and branched alkenyl or alkynyl groups containing from five to ten carbon atoms. More preferred alkenyl and alkynyl groups are straight chain alkenyl or alkynyl groups containing from two to six carbon atoms and branched alkenyl or alkynyl groups containing from five to eight carbon atoms. The term "cycloalkenyl" refers to the cyclic analog of an alkenyl group, as defined above. Preferred cycloalkenyls include cycloalkenyl rings containing from three to eight carbon atoms, and more preferably, from three to six carbon atoms. "Alkenyl", "alkynyl" and "cycloalkenyl", as used herein, include unsubstituted alkenyl or alkynyl radicals, those radicals that are partially or fully halogenated and those radicals substituted with one to four, preferably one or two, substituents from halo, amino, cyano, nitro, methoxy, ethoxy and hydroxy.

The term "aryl" refers to an aromatic carbocyclic radical having from 5 to 8 carbon atoms if monocyclic and from 8 to 12 carbon atoms if bicyclic. Preferred aryl radicals include phenyl and naphthyl. The term "heteroaryl" refers to any aryl radical in which one or more carbon atoms are replaced with a heteroatom. The terms "aryl" and "heteroaryl" also refer to partially or fully halogenated aryl and heteroaryl groups substituted with halo, alkyl; hydroxyl; nitro; nitro; —COOH; —CO(lower alkoxy); CO(lower alkyl); amino; alkylamino; dialkylamino; alkoxy; —NCOH; —NCO(lower alkyl); —NSO$_2$- Ph(halo)$_{0-3}$, Ph; —O—Ph; naphthyl; —O—naphthyl; pyrrolyl; pyrrolyl subsituted with lower alkyl; pyridyl; pyridinyl; pyrazinyl; pyrimidinyl and pyridazinyl.

As summarized above, in a practice of the invention at least one diazo carbonyl compound and at least one allylic alcohol of structures 1 and 2, respectively (Scheme III), are combined to produce tertiary alcohols of structures 3 and/or 4 in Scheme III. A preferred embodiment employs but is not limited to the use of transition metal catalysts in the form of ligated Rh(II) complexes, for example $Rh_2(OAc)_4$, to produce 3 and a Lewis acid like but not limited to $BF_3 \cdot Et_2O$ to convert 3 to 4. In alternative embodiments the decomposition of the diazo substrate to the corresponding carbene or carbenoid involves catalysis by complexes of: Cu(II), Mn(II), Fe(II), Co(II), Ni(0), Ni(II), Zn(II), Mo(II), Ru(II), Ru(III), Bronsted and Lewis acids, thermolysis, and/or photolysis. The derived tertiary alcohols of structure 4 are further manipulated by standard chemical procedures to produce acetals of structure 8 and the corresponding open chain congeners of structure 9. The later are utilized in the furanosylation process and total syntheses described below.

structures 5 and 6 respectively (Scheme IV), to produce indolocarbazoles of structure 7. A preferred embodiment employs but is not limited to the use of transition metal catalysts in the form of ligand Rh(II) complexes, for example $Rh_2(OAc)_4$, in a solvent capable of solvating the substrates such as $CH_2Cl_2$, pinacolone, and/or $CH_3CN$. The reaction is carried out under conditions such that products are formed at a convenient rate such as for exanple about 20–30 minutes at reflux. In alternative embodiments initiating the process via decomposition of the diazo substrate to the corresponding carbene or carbenoid involves catalysis by complexes of: Cu(II), Mn(II), Fe(II), Co(II), Ni(0), Ni(II), Zn(II), Mo(II), Ru(II), Ru(III), Bronsted and Lewis acids, thermolysis, and/or photolysis.

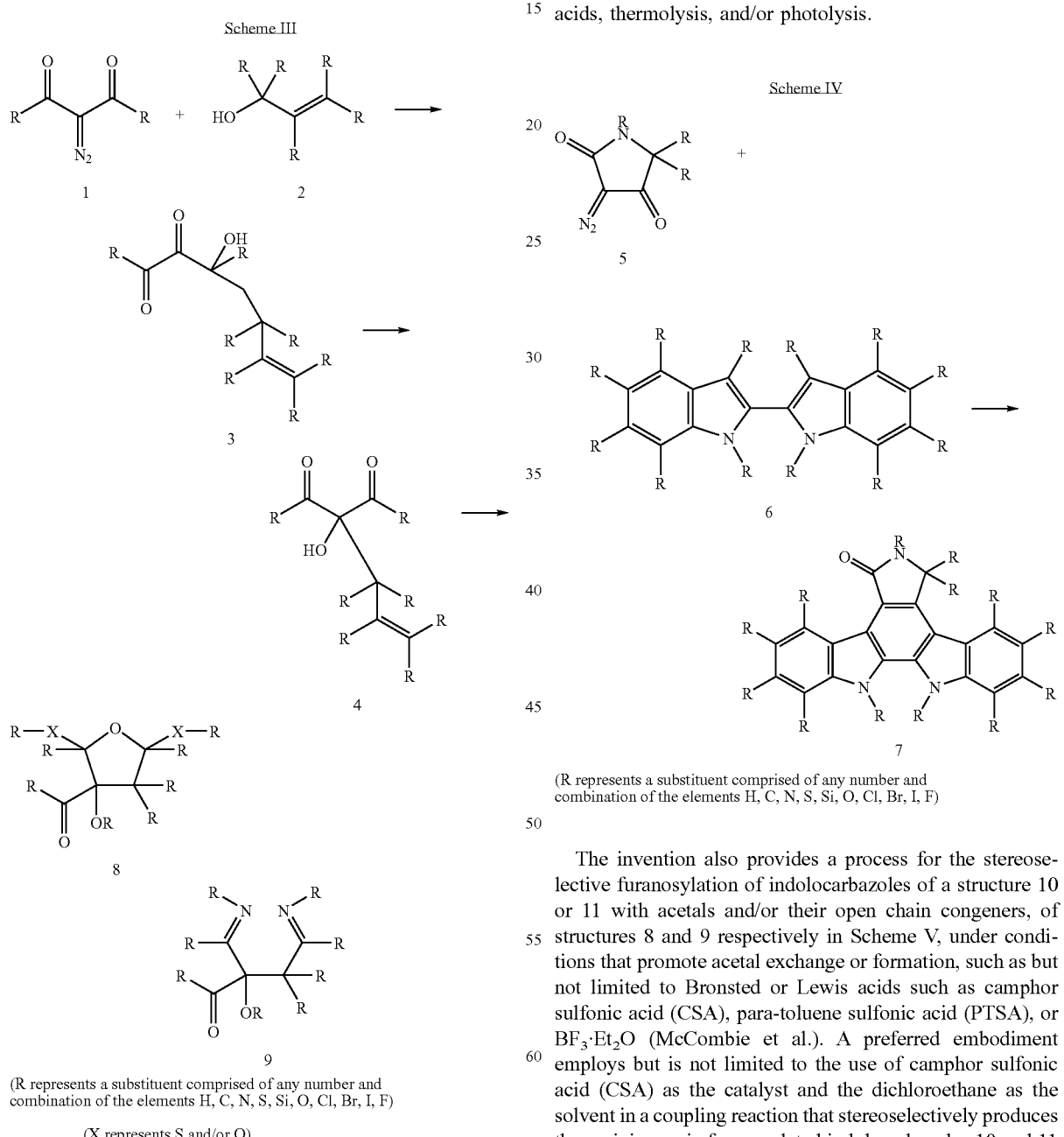

(R represents a substituent comprised of any number and combination of the elements H, C, N, S, Si, O, Cl, Br, I, F)

(X represents S and/or O)

The invention also provides a process for coupling at least one diazo carbonyl compound and at least one biindole, of The invention also provides a process for the stereoselective furanosylation of indolocarbazoles of a structure 10 or 11 with acetals and/or their open chain congeners, of structures 8 and 9 respectively in Scheme V, under conditions that promote acetal exchange or formation, such as but not limited to Bronsted or Lewis acids such as camphor sulfonic acid (CSA), para-toluene sulfonic acid (PTSA), or $BF_3 \cdot Et_2O$ (McCombie et al.). A preferred embodiment employs but is not limited to the use of camphor sulfonic acid (CSA) as the catalyst and the dichloroethane as the solvent in a coupling reaction that stereoselectively produces the regioisomeric furanosylated indolocarbazoles 10 and 11 in about 80% yield. The derived indolocarbazoles of structure 10 are manipulated by standard chemical procedures to produce 14 (K252a).

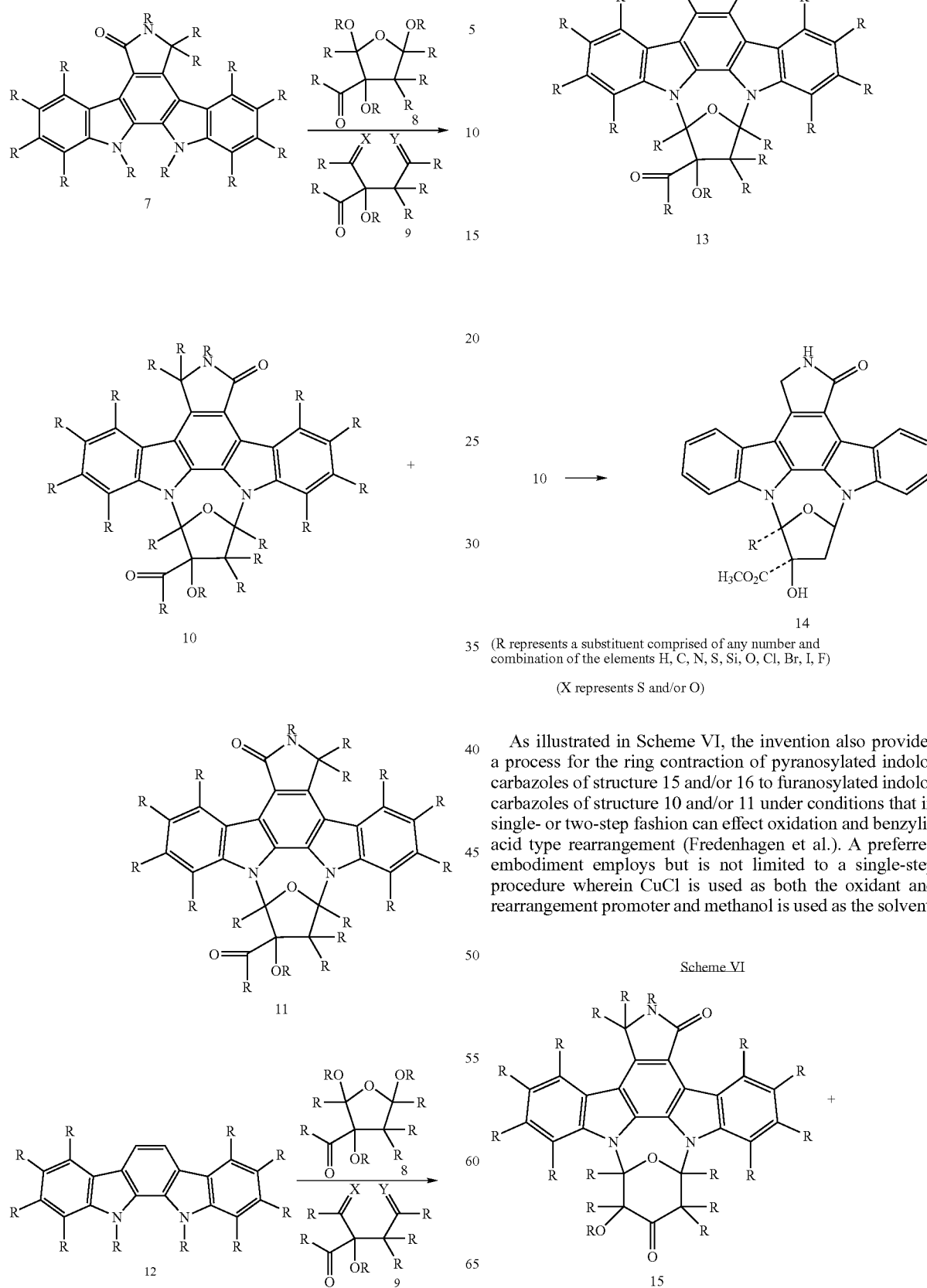

(R represents a substituent comprised of any number and combination of the elements H, C, N, S, Si, O, Cl, Br, I, F)

(X represents S and/or O)

As illustrated in Scheme VI, the invention also provides a process for the ring contraction of pyranosylated indolocarbazoles of structure 15 and/or 16 to furanosylated indolocarbazoles of structure 10 and/or 11 under conditions that in single- or two-step fashion can effect oxidation and benzylic acid type rearrangement (Fredenhagen et al.). A preferred embodiment employs but is not limited to a single-step procedure wherein CuCl is used as both the oxidant and rearrangement promoter and methanol is used as the solvent.

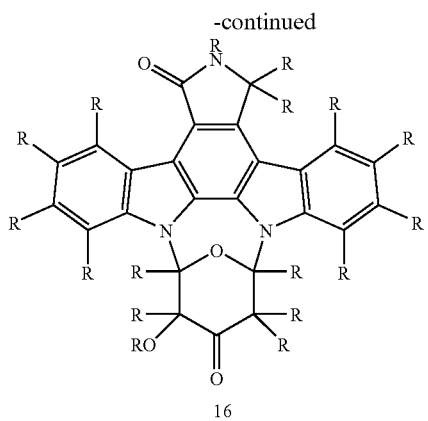

16

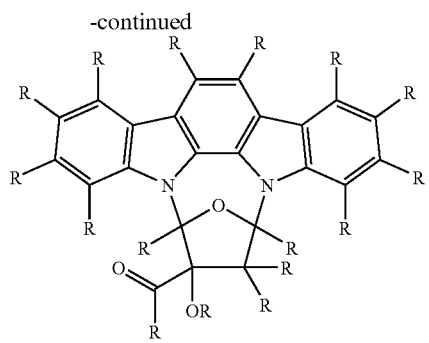

13

(R represents a substituent comprised of any number and combination of the elements H, C, N, S, Si, O, Cl, Br, I, F)

The invention correspondingly provides a process for the ring expansion of furanosylated indolocarbazoles of structure 10 and/or 11 to the pyranosylated congeners of structure 15 and/or 16 illustrated in Scheme VII below (Ootsuka et al.). A preferred embodiment employs, but is not limited to, a multistep procedure wherein 10 and/or 11 is first reduced with $LiBH_4$ and then the derived diol is oxidized. The resulting intermediate compound is then subjected to a Bronsted or a Lewis acid such as camphor sulfonic acid (CSA), para-toluene sulfonic acid (PTSA), or $BF_3 \cdot Et_2O$ to promote ring expansion. $BF_3 \cdot Et_2O$ is used in some preferred embodiments.

Scheme VII

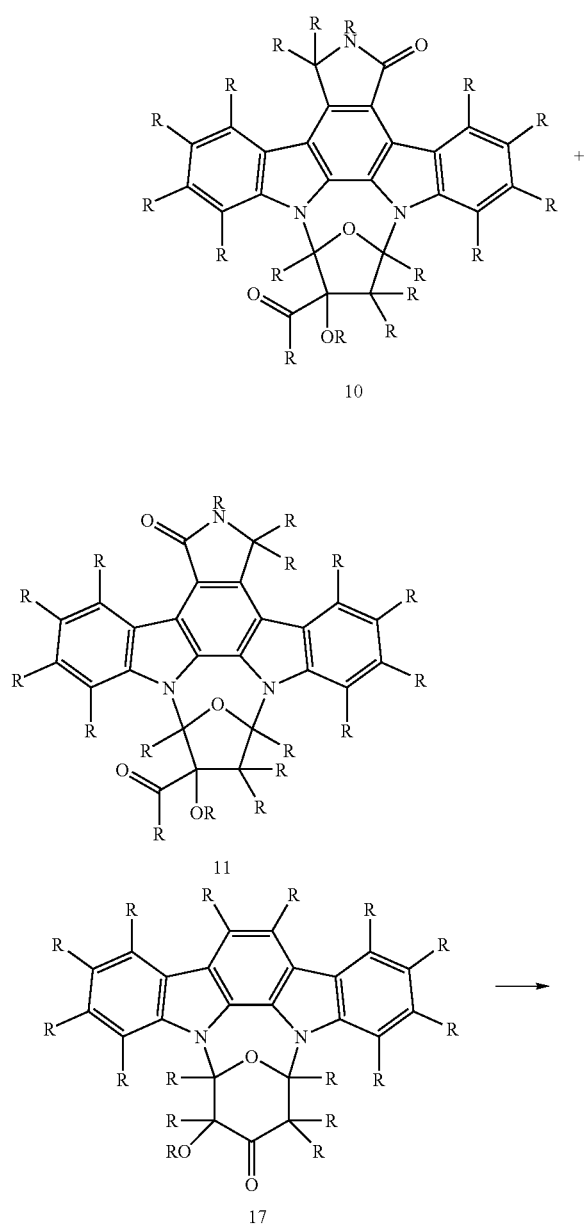

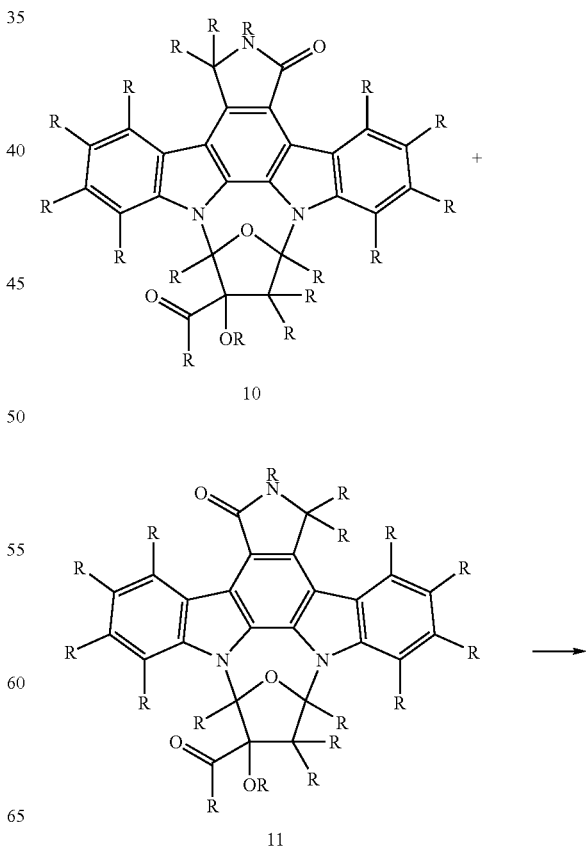

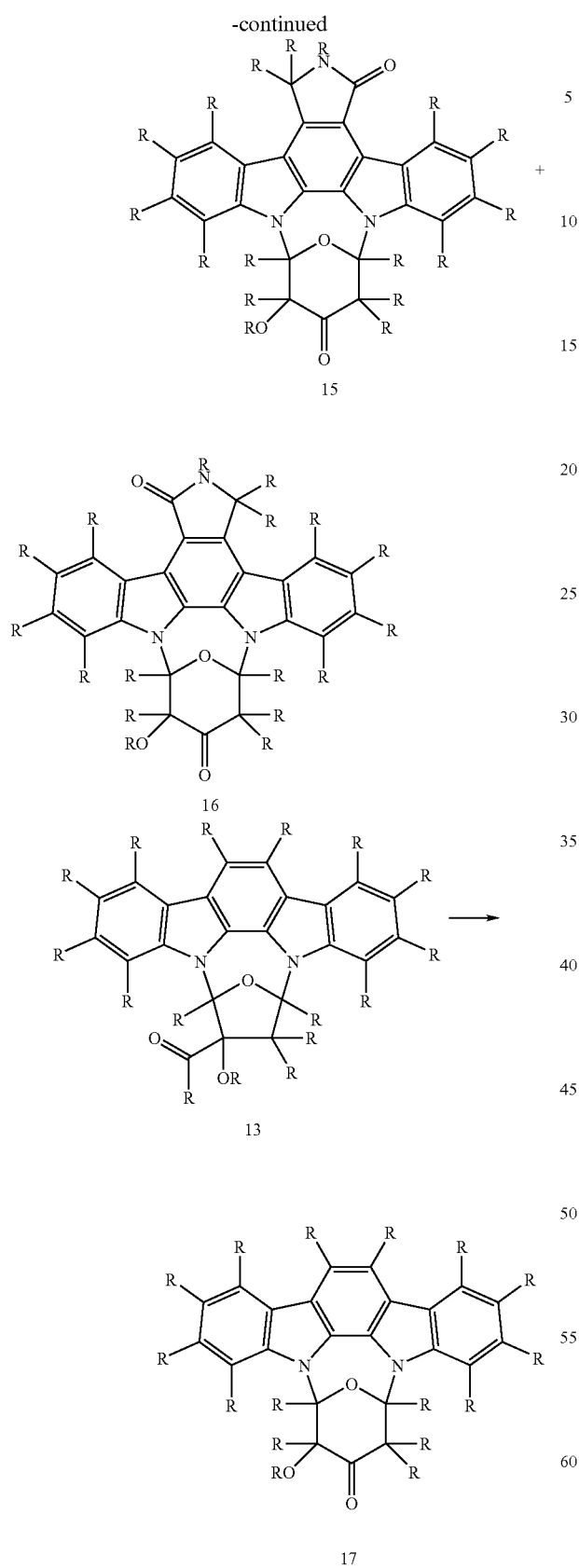
(R represents a substituent comprised of any number and combination of the elements H, C, N, S, Si, O, Cl, Br, I, F)
It is an advantage of the invention that the combined processes provide efficient access to useful indolocarbazoles such as (+)- and (−)-K252a, (+)- and (−)- RK-286c, (+)- and (−)-MLR-52, (+)- and (−)-staurosporine, and the like depicted below.
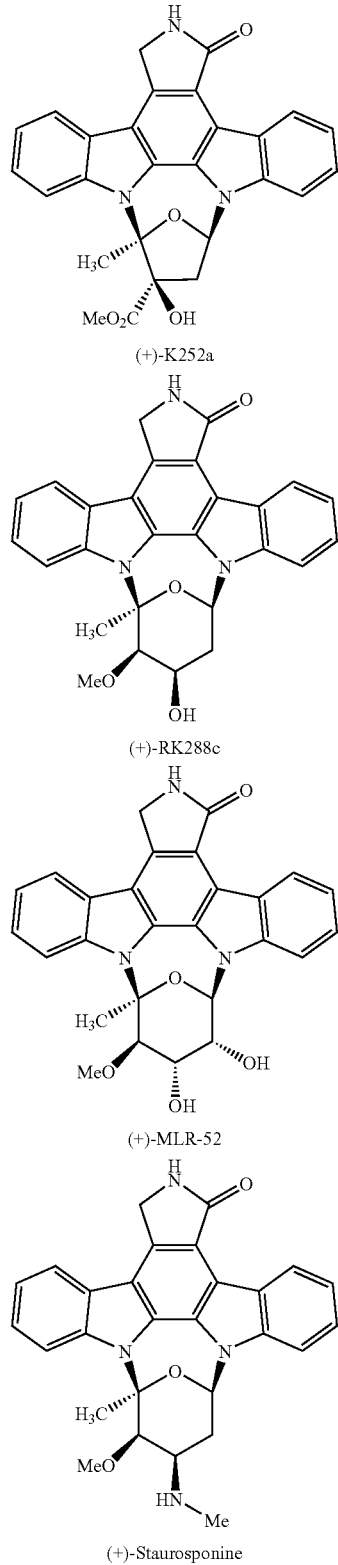

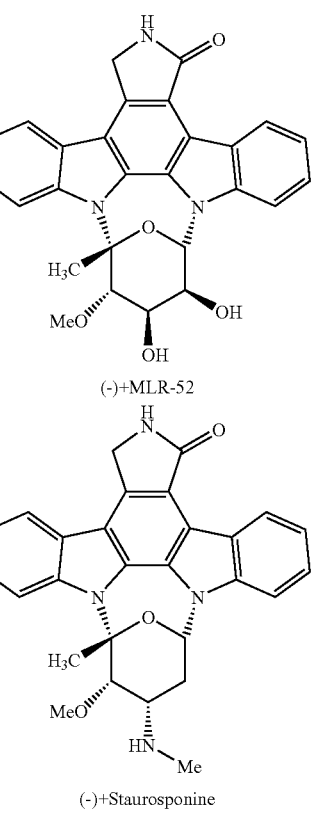

(-)+K252a (-)+RK288c (-)+MLR-52

(-)+Staurosponine

EXAMPLES

The following are presented to further illustrate and explain the present invention and should not be taken as limiting in any regard. Unless otherwise indicated, all parts and percentages are by weight and are based on the weight of the components at the indicated stage of processing. Rotations on indolocarbazole were obtained on methanol solutions. Compound structural assignments were in accord with infrared and high-field $^1$H (500 MHz) and $^{13}$C (125 or 62.5 MHz) NMR spectra, as well as appropriate parent identification by high-resolution mass spectrometry.

EXAMPLE 1

Enantioselective Preparation of Tertiary Alcohols

This example describes a novel rhodium-catalyzed C—C bond forming reaction that allows asymmetric access to 21 (95% ee) and 22 (93% ee) in only two and three steps from methyl acetoacetate (18) (Scheme VIII). In this scenario α-keto ester 21 was produced from the rhodium-catalyzed decomposition of 19 in the presence of S-(+)-1-buten-3-ol (20) (Wood et al.). In the event, complete consumption of 19 was observed after only 20 minutes of reflux in benzene. Proton NMR analysis of the crude reaction indicated the clean formation of a product similar to 19; however, the characteristic methyl ketone singlet had shifted from 2.2 to 1.5 ppm. Clearly the allyloxy or allyloxonium ylide intermediate had undergone [3,3 sigmatropic rearrangement to alcohol (+)-21 (66% yield) (Pirrung et al.). Completion of the tandem rearrangement protocol was achieved by exposing (+)-21 to BF$_3$·Et$_2$O which promoted a clean [1,2]-allyl migration to furnish (−)-22 in 74% yield. In subsequent studies, improved yields were obtained by conducting the tandem rearrangement in one pot. Thus, introducing an equivalent of BF$_3$·Et$_2$O into the cooled [3,3] reaction allows isolation of (−)-22 in an overall yield of 75%.

Scheme VIII

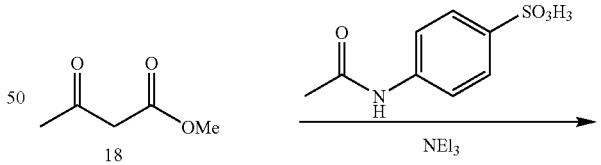

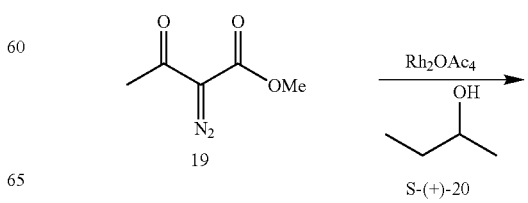

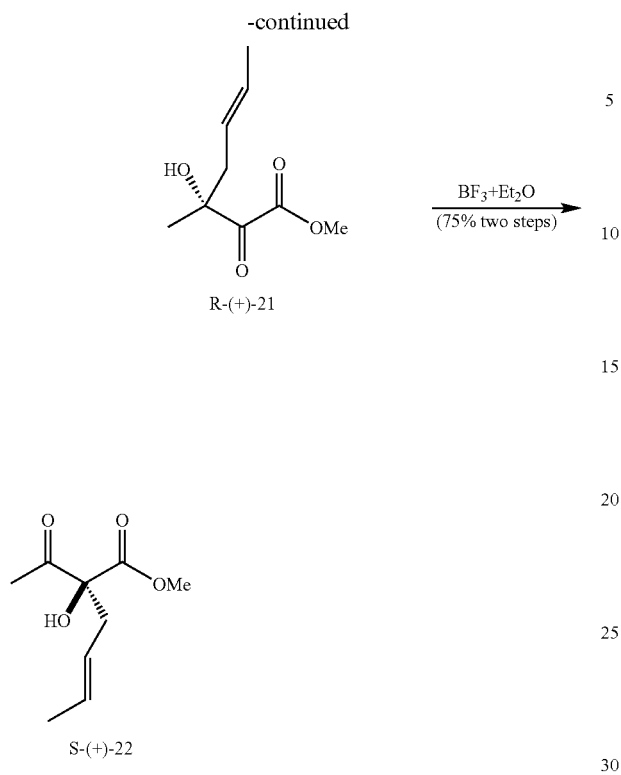

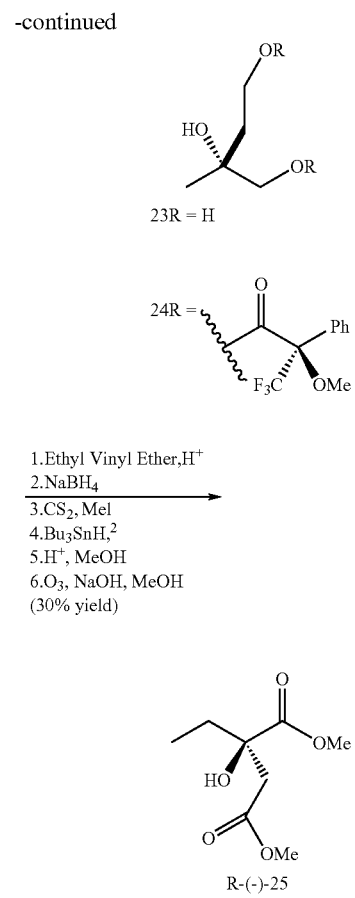

With an approach firmly established, a chemical correlation study was initiated to confirm both the sense and degree of asymmetric induction for the tandem rearrangement. Analysis of the purified products from both the [3,3] (i.e., (+)-21) and [1,2] (i.e., (−)-22) rearrangement via proton NMR in the presence of Eu(hfc)$_4$ gave the first indication that each step was proceeding with a high degree of stereoselectivity. Conversion of (+)-21 to 23 as outlined in Scheme IX, followed by comparison of the derived bis Mosher ester (24) to samples prepared from S-(+)- and R-(−)-ciramalic acid, established that S-(+)-20 (98% ee) had furnished R-(+)-21 (95% ee). Stereoselectivity in the [1,2] shift was established by degradation of (−)-22 to R-(−)-25 followed by DIBAL reduction and proton NMR analysis of the corresponding bis Mosher ester. While the Mosher ester analysis established an ee of 92%, the observation of R-(−)-25 in the degradation proved the absolute stereochemistry in 22 as S.

Having established the degree and sense of asymmetric induction the asymmetric synthesis of the requisite acetals 26 and 27 was begun. Thus, reductive ozonolysis of 22 followed by acetal formation provided a ternary mixture. Spectral identification of the isolated products indicated the presence of methyl ketone 26 and furanoses (+)-27a and (+)-27b (Scheme X).

Scheme X

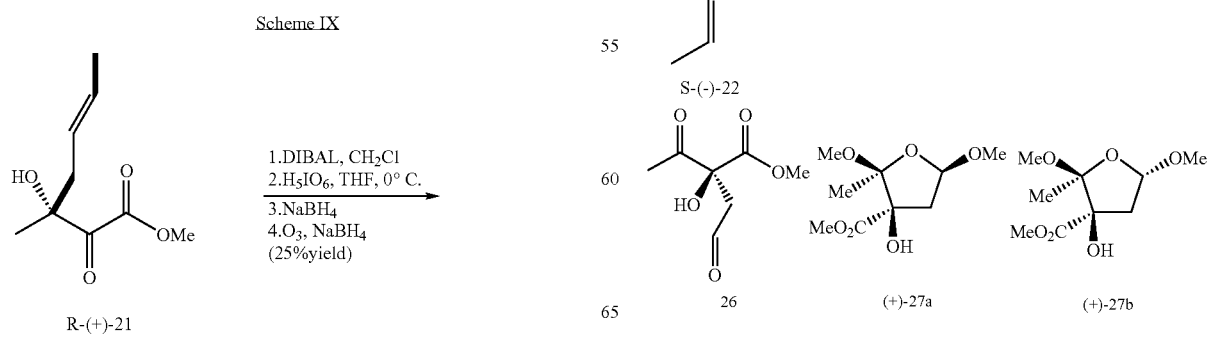

EXAMPLE 2

Preparation and Furanosylation of Indolocarbazoles The Synthesis of K252a

This example describes the coupling of diazolactams 28 and 2,2'-biindole 29 to produce an intermediate that undergoes cycloaromatization to furnish the indolocarbazoles 30. Application of this strategy allows efficient access to both the parent aglycone (30a) and the selectively protected derivatives (30b–c). Of the latter, 30c is employed in the total synthesis of K252a. Overall, preparation of the enantioenriched furanoses 27 (described in Example 1 above) and aglycon unit 30c and their conversion to 14 require only eleven synthetic operations with a longest linear sequence of seven steps.

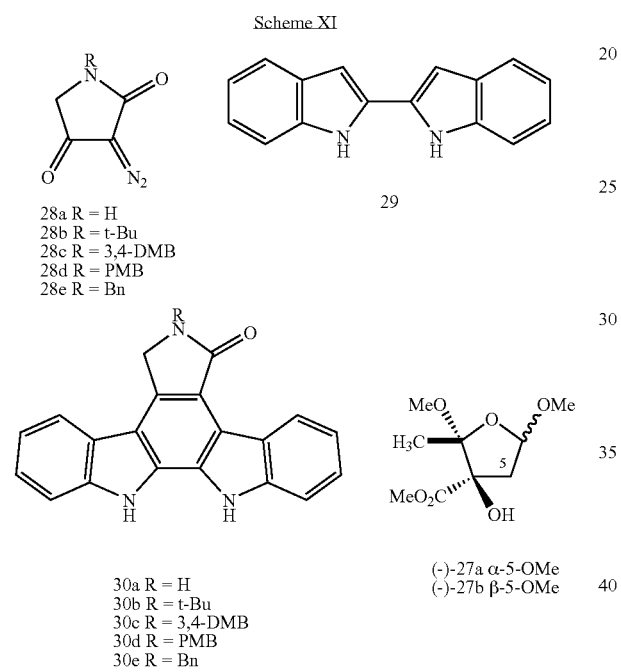

The feasibility of the carbenoid approach to 30 was initially assessed by reaction of 28a (1.0 equiv) with indole (3.0 equiv) in the presence of catalytic $Rh_2(OAc)_4$ (0.01 equiv, Scheme XII). After only 12 h, TLC analysis indicated complete consumption of 28a and standard work-up and isolation procedures furnished 31 in 65% yield. Similar conditions proved ineffective for the coupling of 28a with 29, and it was only after considerable experimentation that a procedure was developed which provided satisfactory yields of 30a. The use of degassed pinacolone provided critical as this solvent was found to be both compatible with the carbenoid chemistry and capable of solvating the diindole substrate. Under these conditions the coupling of 28a and 29 proceeded directly to 30a (K252c) in 27% yield. Presumed intermediate 32 and 33 were not apparent by TLC or NMR analysis of the crude reaction mixture. In an attempt to complete the synthesis, the cycloglycosidation of 27 with 30a revealed a tendency of the latter to alkylate at the amide nitrogen; thus, selectively protected aglycones 30b–e were employed. Preparation of the corresponding diazolactams 28b–e, followed by reaction with 29 in the presence of $Rh_2(OAc)_4$ (0.1 equiv) established that several protecting groups can withstand the carbenoid conditions and that the best yields (50–62%) are obtained within the benzyl class (e.g., 28c,d,e⊘30c,d,e Scheme XII). To provide the most flexibility in the eventual deprotection 3,4-dimethoxybenzyl protected aglycone 28c was employed

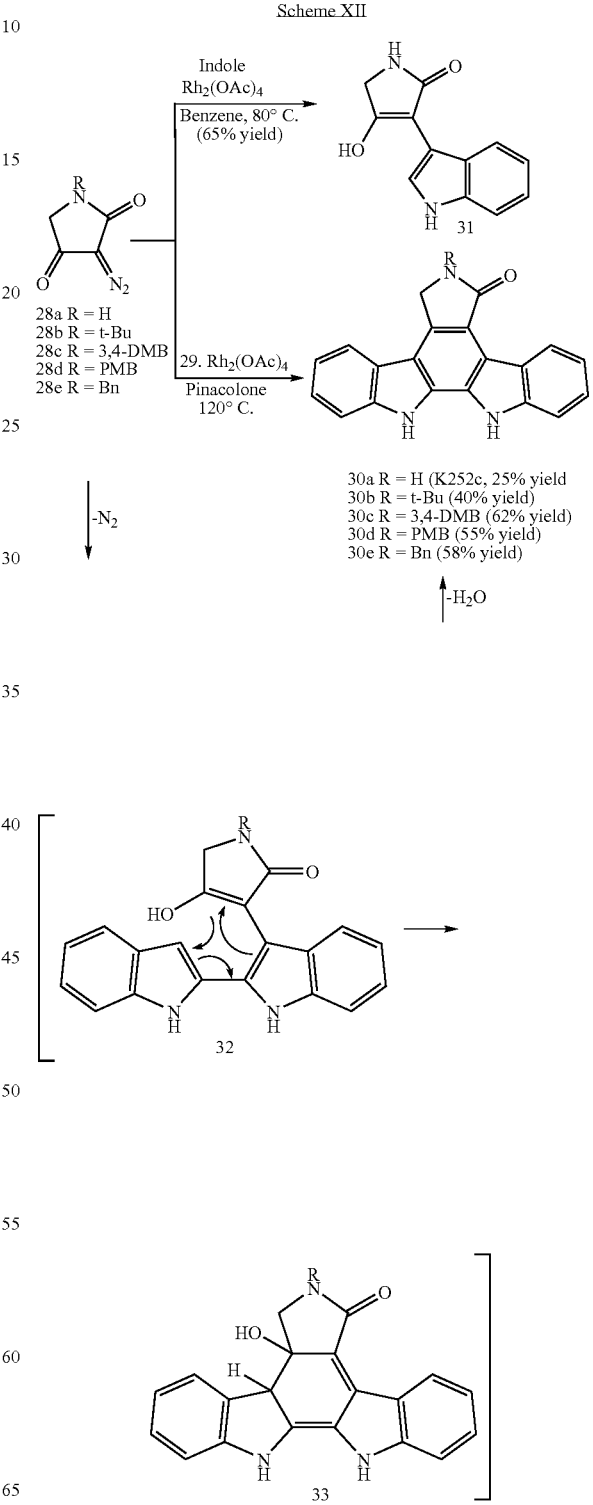

Having gained efficient access to 30c, attention was turned to the preparation of the furanose components (27). To this end, a novel tandem rearrangement protocol was developed that combines methyl 2-diazo-3-oxobutyrate (19) and S-(+)-1-buten-3-ol (20) to furnish (−)-22 in a single-pot (92% ee, yield). Reductive ozonolysis of (−)-22 followed by acid promoted cyclization in methanol produced (+)-27a and (+)-27b in good yield.

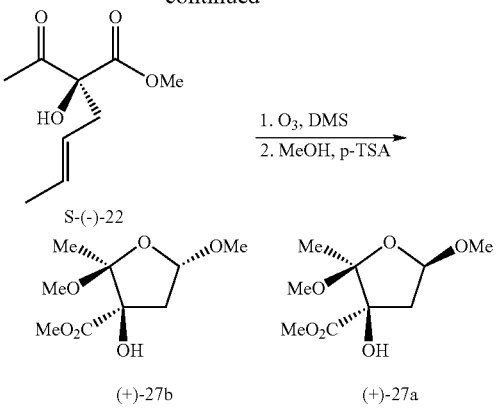

Scheme XIII

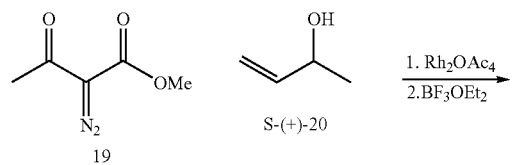

With both (+)-27 and 30c in hand the cycloglycosidative coupling was investigated. Of several conditions reported by McCombie, et al., for related transformations, camphorsulfonic acid in 1,2-dichloroethane was found to be in catalyst and solvent of choice. In the event, 30c and (+)-27a and 27b combined rapidly to form two regioisomeric pairs of open chain monoamino acetal diastereomers (34 and 35). Prolonged heating of the quaternary mixture induced cycloglycosidation to only two of the four possible diastereomers.

Scheme XIV

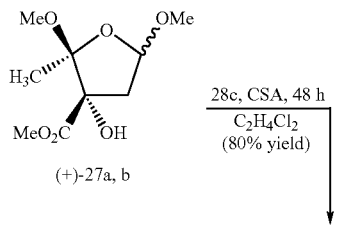

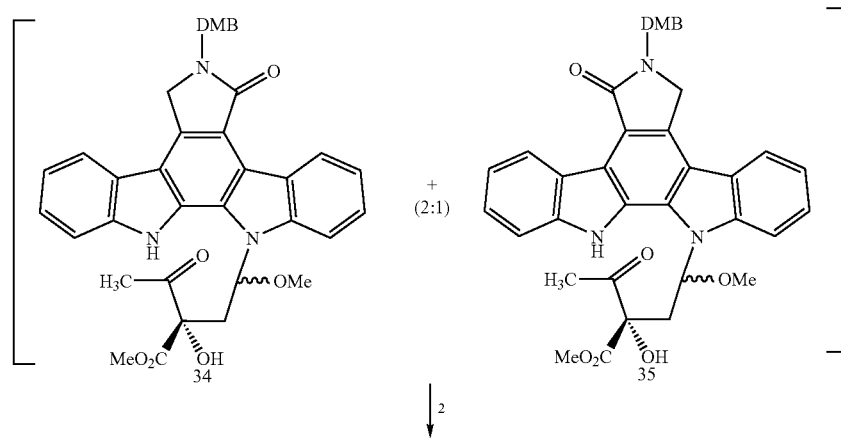

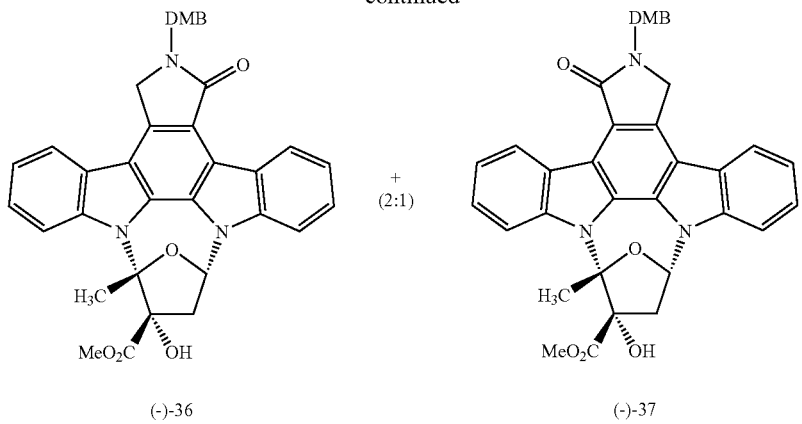

(-)-36      + (2:1)      (-)-37

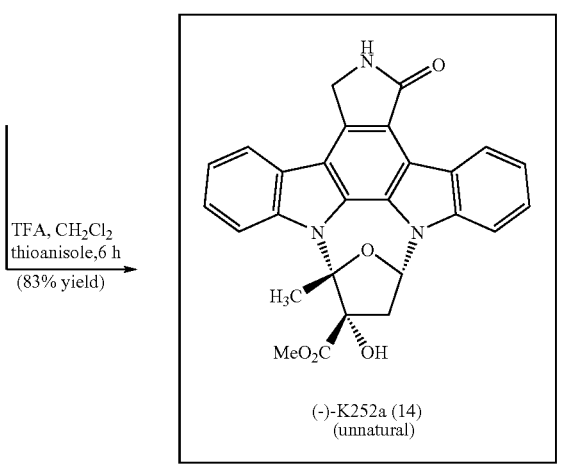

TFA, CH$_2$Cl$_2$
thioanisole, 6 h
(83% yield)

(-)-K252a (14)
(unnatural)

Preliminary assignment of structure was based on $^1$H NMR analysis which indicated that the reaction had produced the regioisomeric products (−)-36 (55% yield) and (−)-37 (25% yield). The observed formation of (−)-14 upon deprotection of (−)-36 under standard conditions (TFA/CH$_2$/thioanisole) established the cycloglycosidation as both regio- and stereoselective for the natural configuration. Comparison of synthetic (−)-14 to material derived from natural sources established its identity as the unnatural enantiomer of K252a.

Total synthesis of the natural enantiomer (i.e., (+)-14) was effected in an analogous fashion using 28c and (−)-27a and (−)-27b as coupling partners (Scheme XV). The latter compound was prepared via the tandem [3,3]/[1,2] rearrangement protocol (described in Example 1 above) using R-(−)-1-nonen-3-ol (38) as the source of asymmetry.

Scheme XV

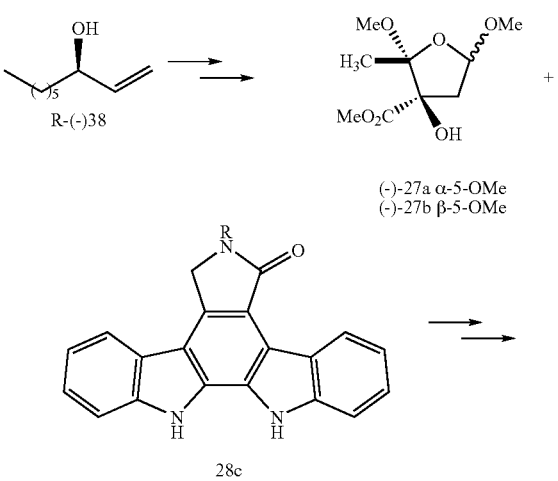

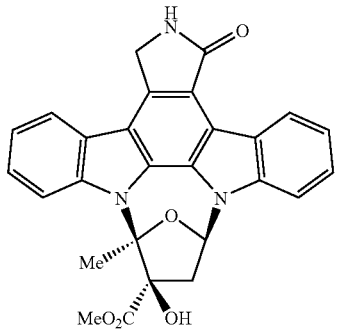

14 (K252a)

In summary, application of a novel carbenoid mediated synthesis of K252c coupled with a highly selective tandem (3,3)/(1,2) rearrangement protocol provides efficient access to both (+)- and (−)-K252a.

EXAMPLE 3

Furanosylation of Alternative Indolocarbazoles and the Interconversion of Furanosylated and Pyranosylated Indolocarbazoles This example reports results wherein an indolocarbazole simpler than that described Example 2 is subjected to furanosylation. The derived product 40 is further manipulated into a ring-expansion substrate 41 or 42 that undergoes conversion to the corresponding pyranosylated indolocarbazole 43 or 44, respectively (Stoltz et al. 1995). It is further demonstrated in this example that the α-hydroxy ketone congener 43 undergoes facile oxidative ring contraction to the furanosylated indolocarbazole upon exposure to CuCl in methanol (Stoltz et al. 1996).

For the furanosylation, indolo [2,3-a]carbazole (39) was coupled with 27a and 27b in a manner similar to that employed in the synthesis of K252a described in Example 2. This coupling again provided highly stereoselective and produced 40 as the only isolable product in 85% yield.

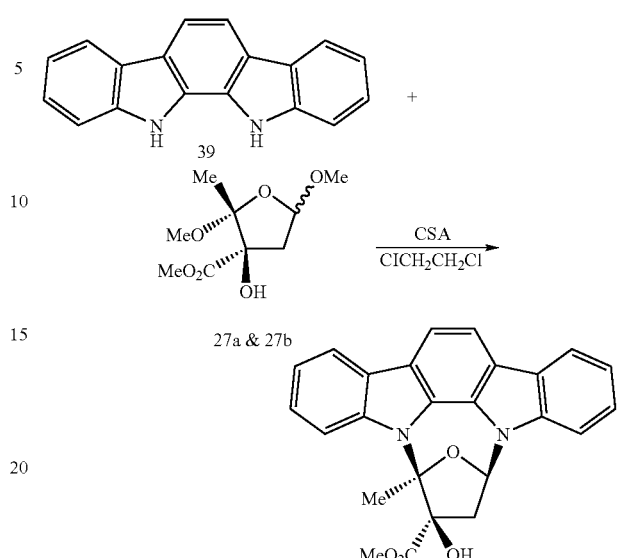

Turning to the ring expansion, it was soon discovered that transformation of 40 into aldehyde 41 followed by treatment with BF$_3$·Et$_2$O results in a regio- and stereoselective rearrangement to the pyranosylated indolocarbazole 43. At this stage all that remained for the preparation of 44 was what appeared to be a trivial alkylation of the C(3') hydroxyl. Ketone 43 surprisingly proved quite resistant to methylation under numerous alkylation conditions. In addition, attempts to incorporate directly the methyl substituent by promoting the rearrangement with a source of Me+ (e.g., Meerweinis reagent, TMSOTf/MSOMe, and MeOTf) also failed. Evenutally, these difficulities led to the development of an alternative strategy that targeted dimethyl acetal 42 as the substrate for a ring expansion (Scheme XVII). Although 42 was readily produced under a variety of conditions, its instability to chromatographic purification required the employment of montmorillonite clay K-10 to promote acetal formation. Removal of the clay via filtration, solvent exchange with Et$_2$O, and subsequent treatment with BF$_3$·Et$_2$O resulted in the slow (72 h, 25° C.) conversion of 42 to 44 (50% yield).

Scheme XVII

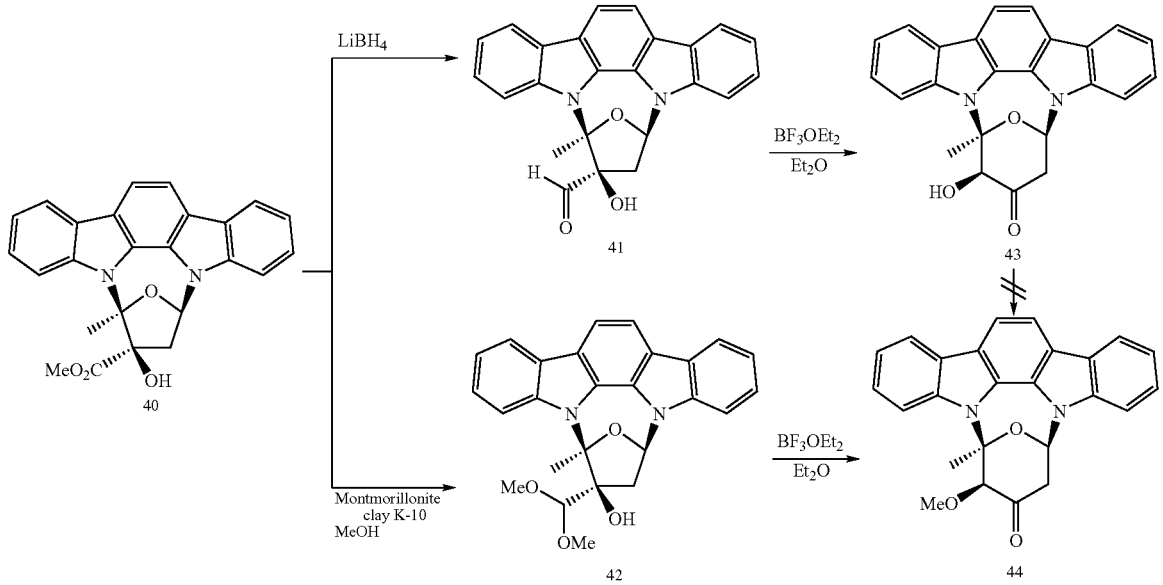

Having rapidly assembled α-methoxy ketone 44, its conversion to the desami-do pyranosylated indolocarbazoles was investigated. To this end, the analogs of RK-286c (46) and TAN-1030a (47) were readily prepared from 44 under standard conditions using NaBH$_4$ and H$_2$NOH·HCl, respectively (Scheme XVIII).

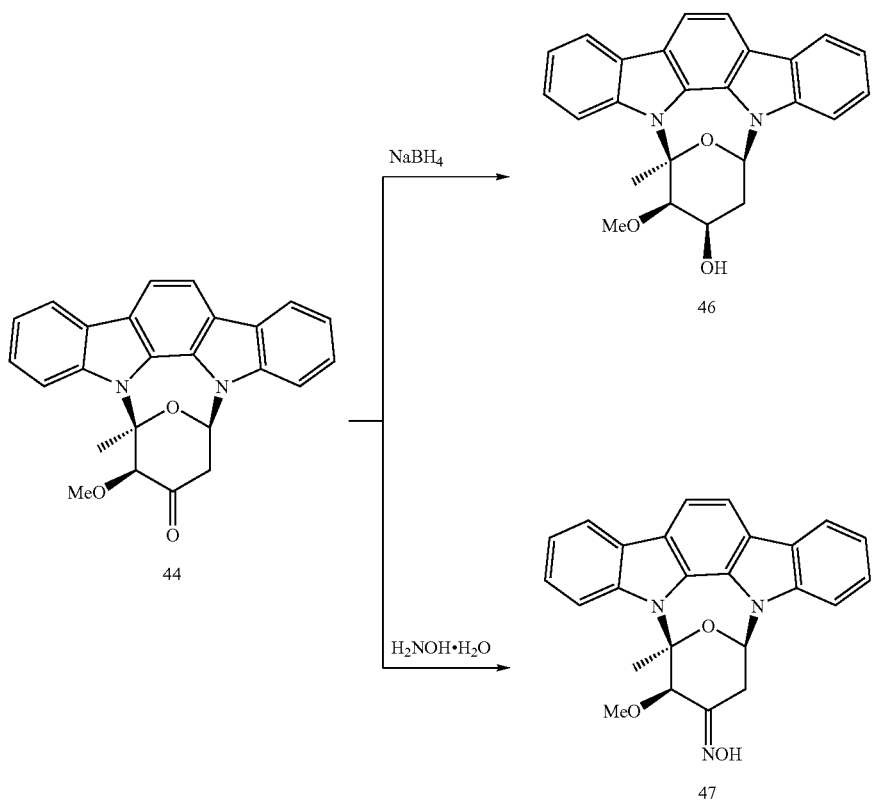

While the above model investigations established the feasiblity of a regio and stereoselective ring expansion, subsequent attempts to alkylate the derived α-hydroxy ketone 43 proved problematic. Of note is the propensity of 43 to undergo loss of the indolocarbazole nucleus as evidenced by isolation of 39 as the major product in many of the alkylation attempts. In an effort to avoid this deleterious event attention was turned to methylation procedures that appeared to proceed under essentially neutral conditions. While these efforts failed to produce any of the desired α-methoxy ketone 44, the conditions comprising CuCl and DCC in MeOH were observed to cleanly convert 43 to 40, the functionalized K252a sugar moiety. Apparanetly these conditions induced either ring contractive α-ketol rearrangement and oxidation (i.e., 43→41→40) or oxidation and ring contractive "benzilic" acid rearragnement (i.e., 43→48→40). While not wishing to be bound to any theory, since α-hydroxy aldehyde 41 failed to undergo conversion to 40 under identical conditions, the latter of these two mechanistic possibilities appears most likely. In addition, subsequent investigations have revealed CuCl in MeOH without added DCC to be the optimal conditions for converting 43 to 40 (95% yield).

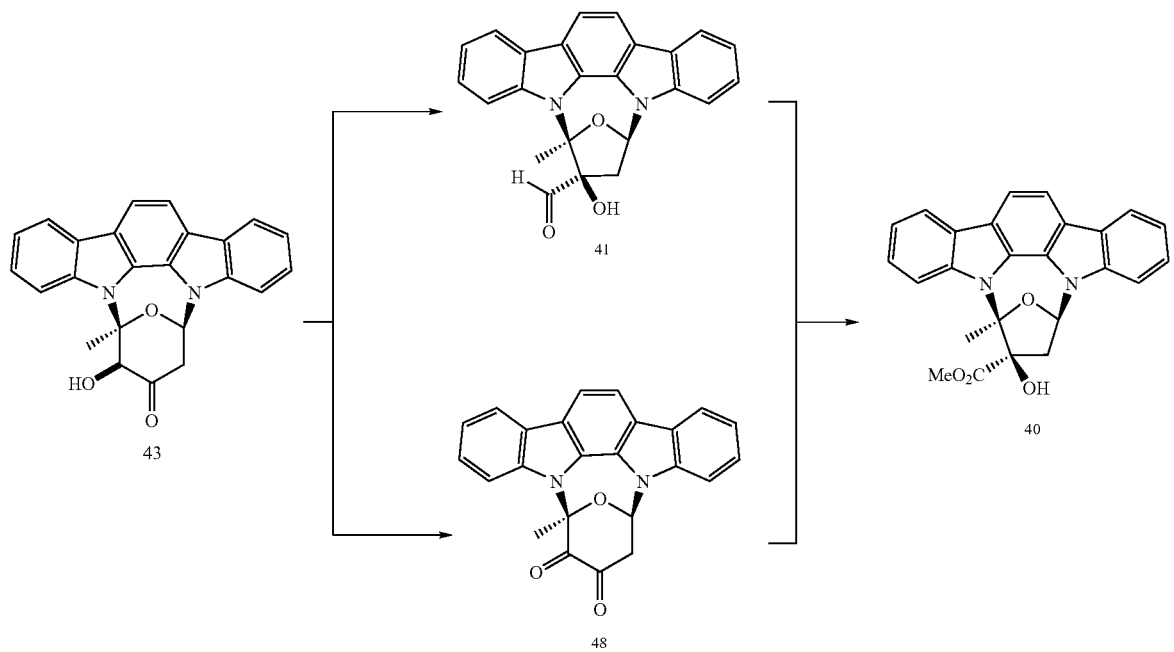

EXAMPLE 4

The Synthesis of Staurosporine, RK-286c, MLR-52, and K252a

This example demonstrates that the tertiary alcohol and indolocarbazole synthesis, the indolocarbazole furanosylation, and the ring-expansion protocol described in the above Examples can be used to prepare pyranosylated indolocarbazoles that are suited for conversion to staurosporine (49) RK-286c (50), MLR-52 (51), and K252a, (14) (Link et al.).

The synthesis of 49–51 began by converting the K252a precursor (36, described above in Example 2) to the corresponding aldehyde via LiBH$_4$ reduction and then Moffatt oxidation (63% overall, Scheme XX). Guided by the α-ketol rearrangement results described above, 50 was exposed to BF$_3$·Et$_2$O and the reaction allowed to stir at room temperature for 3 h. Given that the proposed ring-expansion of 50 to 51 coupld proceed to a mixture of regio- and stereoisomeric products, treatment of (+)-50 with BF$_3$·OEt$_2$ in Et$_2$O (2.2 equiv, 25–30° C., 24 h) surprisingly produces a single product, (+)-51, in 85% yield. The regio- and stereochemical outcome of this reaction, which were confirmed by spectral comparison to a closely related model and the conversion of (+)-51 to (30)-50 (vide infra).

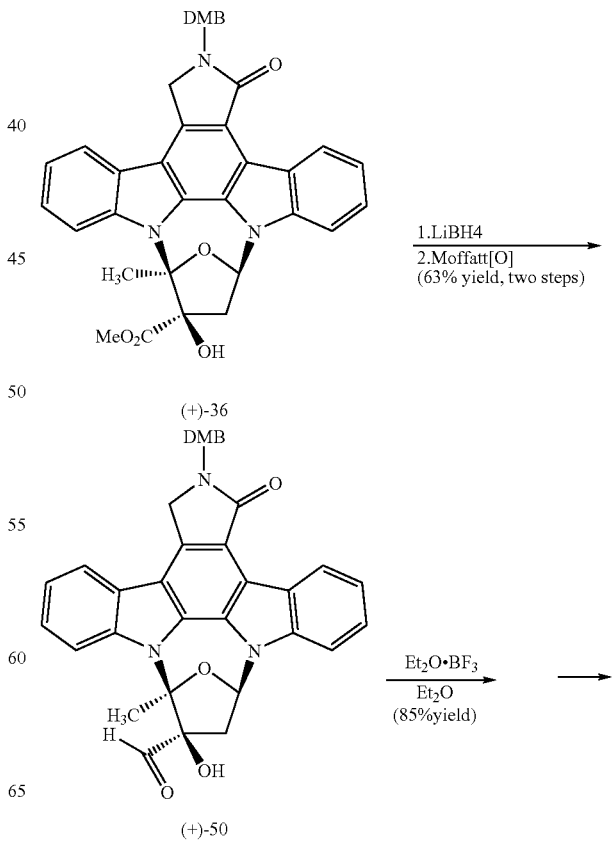

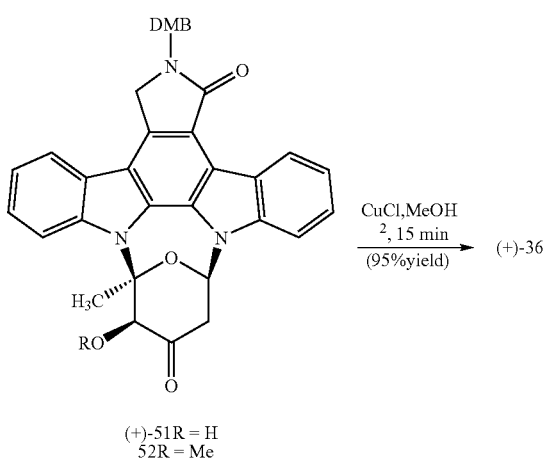

As expected from the data presented in Example 3, attempts to methylate 51 were unproductive and again led to the observation that exposure of (+)-51 to CuCl in MeOH results in a highly stereoselective oxidation/ring-contraction sequence that produces (+)-36 in 95% yield.

Turning from the potentially biomimetic synthesis of (+)-K252a to the synthesis of 49–51, it was discovered that (+)-51 undergoes selective conversion to (+)-54 upon sequential treatment with NaBH₄ and NaH/MeI. Having installed all of the functional groups common to (+)-50–51, the approach diverged into the synthesis of (+)-RK286c and (+)-MLR-52. The former was completed via deprotection of (+)-54 (TFA/anisole) while the latter required a three-step sequence that was initiated by exposing (+)-54 to Martin's sulfurane. Oxidation of the derived olefin with OsO₄ followed by deprotection of the resultant diol (+)-55 produced (+)-51 (Scheme XXI).

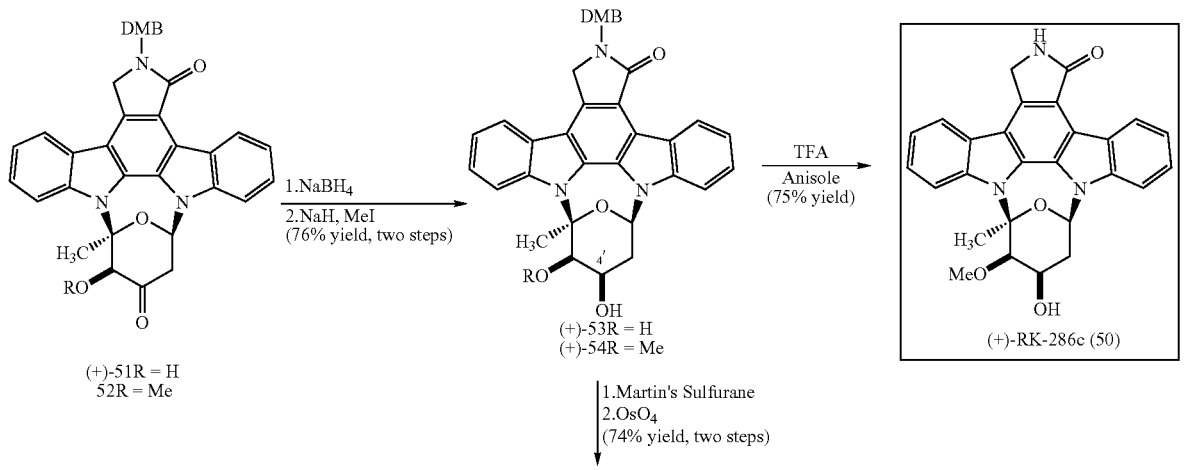

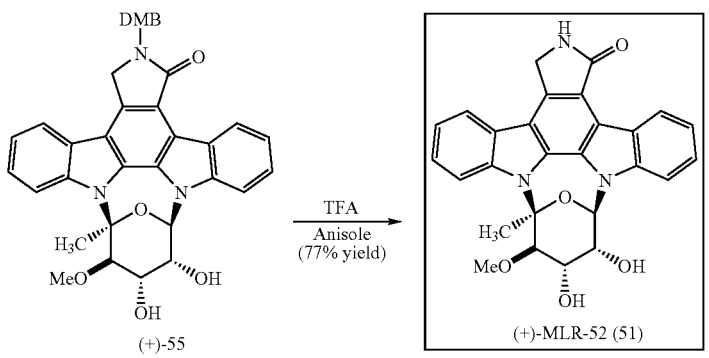

The inability to prepare α-methoxy keton 52 guided an approach to staurosporine along a route wherein the 4' nitrogen is introduced via conversion of (+)-51 to the corresponding oxime (−)-56 (H₂NOH·HCl, NaOAc, Scheme XXII). Crucial for the success of this approach is the fact that (−)-56, unlike ketone (+)-51, readily undergoes alkylation to the C(3") methyl ether (MeI, KOH, n-Bu₄NBr). Stereoselective reduction of the derived methoxy oxime (−)-57 (H₂, PtO₂) to the corresponding primary amine ((+)-58) followed by monomethylation (HCO₂COCH₃, BH₃·DMS) and deprotection (TFA) produced (+)-staurosporine (49).

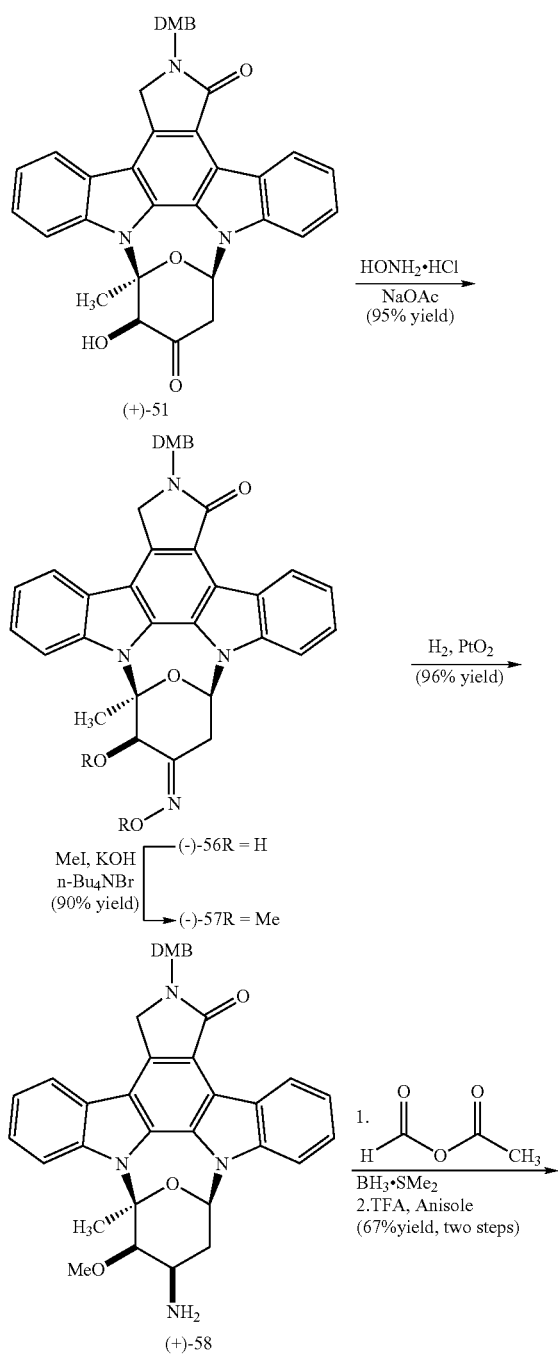

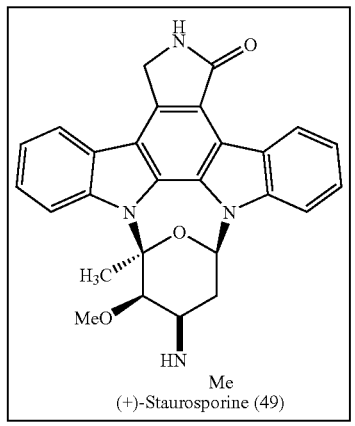

(+)-Staurosporine (49)

EXAMPLE 5

Experimental Procedures for Selected Compounds in Examples 1–4

Preparation of 21. (R)-3-Hydroxy-3-methyl-2-oxo-5-heptenoicacidethylester 2.1323 g (15.00 mmol) 2-diazomethylacetoacetate are dissolved in 75 ml benzene (1 neck 100 ml flask). Under stirring 1.0816 g (15 mmol; 1.3 ml) (S)-(+)-butanol are added to the solution. After addition of 66.3 mg (0.15 mmol; 0.01 eq.) Rh₂(OAc)₄ the flask is immersed into a preheated (100–110° C.) oil bath. The mixture is heated under reflux for 30 minutes. After 1 minute vigourous nitrogen evolution starts and lasts for about 2 minutes. After cooling the mixture the solvent is evaporated and the residue is flashed on silica (4.5×15 cm) using hexane/ethylacetate (20%). 1.66 g (59%) of the product are obtained. This relatively low yield (compared to the 74% obtained in the racemic series) must be due to same impurity (water?) in the butanol. b.p. 65–67°/0.35 mm Hg; IR (thin film/NaCl) 3521.0 (m), 3028.5 (w), 2981.5 (m), 2957.1 (m), 2937.9 (m), 2919.9 (m), 2857.4 (w), 1742.6 (s), 1726.1 (s), 1452.3 (m), 1437.5 (m), 1376.0 (w), 1361.2 (w), 1289.1 (m), 1250.1 (m), 1192.6 (w), 1145.8 (w), 1116.3 (w), 1081.5 (w), 1060.1 (w), 1032.1 (s), 971.9 (m), 920.3 (w), 861.6 (w), 844.7 (w), 814.4 (w), 722.7 (w), 663.1 (w) cm⁻¹; ¹H NMR (500 MHz, CDCl₃) δ5.57 (m, 1H), 5.35 (m, 1H), 3.88 (s, 3H), 3.28 (br.s, 1H), 2,68 (dd, J=7.0, 14.0 Hz, 1H), 2.42 (dd, J=7.7, 14.0 Hz, 1H), 166 (d, J=6.42 Hz, 3H), 1.47 (s, 3H); ¹³C NMR (125 MHz, CDCl₈) δ198.58, 162.78, 130.97, 123.58, 78.30, 52.55, 42.26, 24.15, 17.82; HRMS (CI, isobutane) m/z calc'd for C₉H₁₅O₄ (M+H): 187.0970, found 187.0966; [α]D²²+14.65° (c=1.08, CHCl₃).

Preparation of 22. (S)-2-Hydroxy-2-allylmethylmethylactoacetate 3.35 g (18 mmol) (R)-3-hydroxy-3-methyl-2-oxo-5-heptenoicacidethyl-ester are dissoved in 180 ml dichloromethane and treated with 2.554 g (18 mmol; 2.21 ml) BF₈·OEt₂. The reaction mixture is stirred 2 hours at 25° C. (TLC control). The solvent is evaporated and the residue flashed on silica (4.5×18 cm) using hexane/ethylacetate (20%). 2.868 g (71%) of the product are isolated. IR (thin film/NaCl) 3476.1 (m), 3031.2 (w), 3009.6 (w), 2956.2 (m), 2921.4 (w), 2857.5 (w), 1746.9 (s), 1721.9 (s), 1437.4 (m), 1357.9 (m), 1271.0 (m), 1224.2 (m), 1195.9 (m), 1183.2 (m), 1141.0 (m) 1108.5 (m), 1076.9 (w), 1052.8 (w), 994.6 (w), 972.4 (m), 861.8 (w), 816.7 (w), 798.8 (w) cm⁻¹; ¹H NMR (500 MHz, CDCl₃) δ5.60 (m, 1H), 5.32 (m, 1H), 4.17 (s, 1H), 3.80 (s, 3H), 2.77 (dd, J=6.6, 14.3 Hz, 1H), 2.63 (dd, J=7.6, 14.3 Hz, 1H), 2.28 (s, 3H), 1.65 (d, J=6.5 Hz, 3H); $^{13}$C NMR (125 MHz, CDCl$_3$) δ 204.28, 170.85, 130.59, 122.91, 83.89, 53.16, 38.54, 24.76, 17.94; HRMS (CI, isobutane) m/z calc'd for C$_9$H$_{15}$O$_4$ (M+H): 187.0970, found 187.0969; $[\alpha]D^{22}$ 32.13° (c=1.08, CHCl$_3$). (S)-2-Hydroxy-2-allylmethylmethylacetoacetate (1 pot procedure) 426.5 mg (3.00 mmol) 2-diazomethylacetoacetate are dissolved in 15 ml benzene (1 neck 25 ml flask). Under stirring 237.9 mg (3.3 mmol; 0.286 ml; 1.1 eq.) (S)-(+)-butenol are added to the solution. After addition of 13.3 mg (0.03 mmol; 0.01 eq.) Rh$_2$)OAc)$_4$ the flask is immersed into a preheated (100–110° C.) oil bath. The mixture is heated under reflux for 80 minutes. After 1 minute vigouros nitrogen evolution starts and lasts for 2 minutes. After cooling the reaction mixture 554.5 mg (3.75 mmol; 0.46 ml; 1.25 eq.) BF$_3$·OEt$_2$ are added. The mixture is stirred for 2–3 hours (TLC control) at 25° C. The reaction mixture is passed through silica (2.5×8 cm) using pentane/ether (20) as solvent; 416.9 mg (75%) of the product are isolated.

Preparation of 27. (S)-(+)-Hydroxy furanose and (S)-(–)-methylketonedimethylacetal 1.305 g (700 mmol) (S)-2-hydroxy-2-allylmethylmethylacetoacetate and a trace of sudan red dye are dissolved in 45 ml methanol. After cooling to –78° C. the mixture is treated with O$_3$ until the dye is completely discolored (about 3 minutes). The mixture is purged with argon for 10 Minutes at –78° C. and 20 ml dimethylsulfide are added at that temperature. The dry ice cold bath is replaced with an ice bath which is allowed to thaw (0–20 C.) over a period of 3 hours. The solvent is removed and the crude product dissoved in in 45 ml benzene. After addtion of 20.0 mg (0.105 mmol; 0.015 eq.) p-toluenesulfonic acid and 12 ml methanol the mixture is stirred at 25° C. for 17 hours (until the reaction is completed as judged by TLC). The solvent is evaporated and the product is flashed on silica (4.5×20 cm) using hexane/ethylacetate (20%) as solvent system. 1.69 g (80%) of a mixture (1:1:1) of two furanose diastereomers and the methylketonedimethylacetal is obtained. They can be separated using HPLC. In a first run (stationary phase: SiO$_2$; mobile phase: hexane/dichloromethane/ethylacetate (2:2:1) a mixture of the furanose diastereomer I and the metyhylketone is eluated first followed by the second furanose diastereomer which can be isolated in its pure form. The two component mixture is separated using a different system (stationary phase: SiO$_2$; mobile phase: hexane/i-propanol (10%)). The furanose diastereomer I is eluated as first fraction closely followed by the methylketonedimethyl acetal. Hydroxyfuranose mp 81–82° C.; IR (thin film/NaCl) 3495.1 (m), 2995.3 (m), 2953.2 (s), 2917.2 (s), 2848.3 (m), 1747.11 (s), 1463.77 (m), 1439.35 (m), 1379.1 (m), 1355.2 (w), 1263.5 (s), 1200.0 (s), 1182.1 (m), 1156.1 (m), 1121.86 (s), 1086.1 (s), 1043.7 (m), 1019.3 (m), 973.677 (m), 949.3 (m), 929.7 (m), 892.27 (m), 864.6 (w), 833.7 (m), 802.7 (m), 750.6 (m), 685.5 (m) cm$^{-1}$; $^1$H NMR (500 MHz, CDCl$_8$) δ 5.07 (dd, J=0.6, 5.8 Hz, 1H), 3.79 (s, 3H), 3.42 (s, 3H), 3.38 (br. s, 1H), 3.25 (s, 3H), 3.08 (dd, J=5.8, 14.2 Hz, 1H), 2.06 (d, J=14.2 Hz, 1H), 1.54 (s, 3H); $^{13}$C NMR (125 MHz, CDCl$_3$) δ170.50, 110.55, 103.86, 83.17, 55.56, 52.63, 49.28, 40.56, 15.82; $[\alpha]D^{20}$+112.13° (c=1.06, CHCl$_3$). Methylketone IR (thin film/NaCl) 3450.0 (m), 2988.3 (m), 2953.5 (s), 2915.0 (s), 2849.2 (s), 1746 (s), 1722.3 (s), 1457.5 (m), 1436.4 (m), 1386.7 (m), 1275.0 (m), 1245.2 (m), 1198.0 (m), 1178.1 (m), 1142.1 (s), 1121.0 (s), 1063.3 (s), 1014.2 (w), 998.1 (w), 974.4 (w), 907.4 (w), 830.6 (w), 755.1 (w) cm$^{-1}$; $^1$H NMR (500 MHz, CDCl$_3$) δ4.50 (s, 1H), 4.50 (dd, J=4.8, 6.7 Hz, 1H), 3.78 (s, 3H), 3.34 (s, 3H), 3.29 (s, 3H), 2.43 (dd, J=4.8, 14.5 Hz, 1H), 2.39 (dd, J=6.7, 14.5 H, 1H), 2.28 (s, 3H); $^{18}$C NMR (125 MHz, CDCl$_3$) δ204.04, 170.87, 102.01, 81.80, 54.99, 53.84, 53.22, 38.40, 24.50; $[\alpha]D^{20}$–20.25° (c=0.97, CHCl$_3$). Hydroxyfuranose mp 63–64° C.; IR (thin film/NaCl) 3480.7 (m), 2995.0 (w), 2953.3 (m), 2914.2 (w), 2835.1 (w), 1726.7 (s), 1443.2 (m), 1377.9 (m), 1348.2 (w), 1278.2 (s), 1239.0 (m), 1228.0 (m), 12004. (m), 1181.6 (w), 1165.1 (s), 1127.6 (s), 1114.3 (s), 1092.2 (m), 1084.5 (m), 979.6 (m), 957.5 (m), 948.7 (m), 927.8 (m), 901.5 (m), 871.9 (w), 840.9 (w), 802.9 (w), 755.5 (m), 673.0 (w) cm$^{-1}$; $^1$H NMR (500 MHz, CDCl$_3$) δ5.21 (app. t, J=5.7 Hz, 3H), 3.79 (s, 3H), 3.47 (s, 3H), 3.36 (d, J=1.6 Hz, 1H), 3.27 (s, 3H), 2.84 (ddd, J=1.6, 5.2, 14.3 Hz, 1H), 2.34 (dd, J=6.2, 14.3 Hz, 1H), 1.43 (s, 3H); $^{13}$C NMR (125 MHz, CDCl$_3$) δ172.10, 1089.84, 105.38, 84.46, 56.37, 52.82, 49.00, 40.44, 14.46; HRMS (CI, isobutane) m/z calc'd for C$_8$H$_{13}$O$_5$ (M—CH$_3$OH+H): 189.0763, found 189.0764; $[\alpha]D^{22}$+9.66° (c=1.03, CHCl$_3$).

Preparation of 38. (R)-2-Hydroxy-2-allylhexylmethylacetoacetate 426.5 mg (3.00 mmol) 2-diazomethylacetoacetate are dissolved in 15 ml benzene (1 neck 25 ml flask). Under stirring 469.3 mg (3.3 mmol; 1.1 eq.) (R)-(–)-nonenol are added to the solution. After addition of 13.3 mg (0.03 mmol; 0.01 eq.) Rh$_2$(OAc)$_4$ the flask is immersed into a preheated (100–110° C.) oil bath. The mixture is heated under reflux for 30 minutes. After 1 minute vigouros nitrogen evolution starts and lasts for about 2 minutes. After cooling the reaction mixture 554.5 mg (3.75 mmol; 0.46 ml; 1.25 eq.) BF$_3$·OEt$_2$ are added. The mixture is stirred for 2–3 hours (TLC control) at 25° C. The reaction mixture is passed through silica (2.5×8 cm) using pentane/ether (20%) as solvent; 510.9 mg (66%) of the product are isolated. R)-(–)-Hydroxy furanose and (R)-(+)-methylketonedimethylacetal The same procedure that was employed for the preparation of (S)-(+)-hydroxy furanose and (S)-(–)-methylketonedimethylacetal is used. 1.798 g (7.00 mmol) of (R)-2-hydroxy-2-allylhexylmethylacetoacetate are used as starting material yielding 1.04 g (68%) of the 3 component mixture (1:1:1). Hydroxyfuranose mp 81–82° C.; IR (thin film/NaCl) 3496.4 (m) 2998.9 (m), 2953.3 (m), 2915.1 (m), 2836.9 (m), 1748.9 (s), 1732.9 (s), 1440.3 (m), 1379.3 (m), 1334.7 (w), 1261.7 (s), 1200.7 (s), 1182.7 (m), 1156.9 (s), 1122.5 (s), 1098.5 (s), 1086.5 (s), 1044.3 (m), 1021.1 (m), 975.9s, 94820. (m), 930.7 (m), 893.9 (m), 865.4 (m), 834.9 (m), 802.2 (m), 750.9 (m), 658.7 (m), cm$^{-1}$; $^1$H NMR (500 MHz, CDCl$_3$) δ5.07 (d, J=5.8 Hz, 1H), 3.78 (s, 3H), 3.42 (s, 3H), 3.25 (s, 3H), 3.03 (dd, J=5.8, 14.1 Hz, 1H), 2.05 (d, J=14.1 Hz, 1H), 1.54 (s, 13H); $^{13}$C NMR (125 MHz, CDCl$_3$) δ170.41, 110.46, 103.78, 83.08, 55.47, 52.52, 49.18, 40.49, 15.73; $[\alpha]D^{20}$–122.55° (c=1.10, CHCl$_3$). Methylketone IR (thin film/NaCl) 3452.5 (m), 2993.2 (m), 2954.6 (m), 2934.2 (m), 2917.5 (m), 2848.4 (m), 2838.2 (m), 1748.7 (s), 1723.1 (s), 1437.8 (m), 1359.7 (m), 1275.8 (m), 1245.7 (m), 1198.5 (m), 1178.2 (m), 1144.7 (s), 1124.4 (s), 4065.4 (s), 1015.7 (m), 997.3 (m), 905.2 (m), 829.6 (w), 802.0 (w), 756.0 (w) cm$^{-1}$; $^1$H NMR (500 MHz, CDCl$_3$) δ4.51 (br. s, 1H), 4.50 (dd, J=4.9, 6.6 Hz, 1H), 3.78 (s, 3H), 3.34 (s, 3H), 3.29 (s, 3H), 2.43 (dd, J=4.9, 14.6 Hz, 1H), 2.38 (dd, J=6.6, 14.6 Hz, 1H), 2.28 (s, 3H); $^{13}$C NMR (125 MHz, CDCl$_3$) δ204.00, 170.84, 101.96, 81.76, 54.92, 53.79, 53.18, 38.37, 24.46; $[\alpha]1D^{20}$+19.55° (c=1.12, CHCl$_3$). Hydroxyfuranose mp 63–64° C.; IR (thin film/NaCl) 3486.7 (m), 2994.8 (m), 2954.8 (m), 2918.0 (m), 2836.2 (m), 1732.7 (s), 1442.6 (m), 1378.3 (m), 1346.6 (w), 1276.5 (s), 1243.0 (m), 1229.7 (m), 1199.7 (m), 1183.0 (m), 1165.4 (s), 1126.7 (s), 1115.6 (s), 1086.6 (m), 1049.2 (s), 1020.2 (s), 980.1 (m), 956.6 (m), 626.1 (m), 902.6 (m), 870.2 (w), 840.2 (w), 803.0

(w), 754.6 (m), 673.3 (m) cm$^{-1}$; $^1$H NMR (500 MHz, CDCl$_3$) δ5.21 (app. t, J=5.7 Hz, 1H), 3.79 (s, 3H), 3.47 (s, 3H), 3.36 (br. s, 1H), 3.27 (s, 3H), 2.84 (dd, J=5.3, 14.3 Hz, 1H), 2.34 (dd, J=6.2, 14.3 Hz, 1H), 1.43 (s, 3H); $^{13}$C NMR (125 MHz, CDCl$_3$) δ172.11, 109.86, 105.40, 84.48, 56.39, 52.83, 49.02, 40.46, 14.48; [α]D$^{20}$ –9.00° (c=1.16, CHCl$_3$).

General method for the preparation of 30a–d Dry N$_2$ is bubbled through a mixture of 2,2'-biindole (0.86 mmol), diazo compound 4 (2.2 mmol, 2.5 eq.), Rh$_2$(OAc)$_4$ (0.086 mmol, 0.1 eq.) and 8.6 mL pinacolone, in a 3-neck round bottom flask fitted with a reflux condenser for 2 h. The reaction mixture is then heated to reflux for 8 h. The mixture is allowed to cool to 25° C., the solvent is evaporated, the residue is chromatographed (1:1 EtOAc:Hexanes) to provide (R=3,4-DMB 0.25 g, 0.56 mmol, 65% R=4-PMB 0.22 g, 0.47 mmol, 55%; R=Bn 0.20 g, 0.5 mmol, 58%; R=t Bu 0.13 g, 0.34 mmol, 40%).

Indolocarbazole 30a. IR (thin film/NaCl) 3485.3 (brm), 3456.0 (brm), 3343.1 (brs), 3249.7 (brm), 2979.7 (m), 1654.4 (w), 1600.5 (s), 1578.2 (s), 1465.8 (w), 1446.5 (m), 1385.0 (s), 1364.0 (m), 1335.9 (w), 1225.3 (s) cm$^{-1}$; $^1$H NMR (500 MHz, DMSO-d$_6$) δ11.45 (bs, 1H), 11.29 (bs, 1H), 9.24 (d, J=7.9 Hz, 1H), 8.09 (d, J=7.8 Hz, 1H), 7.77 (d, J=8.2 Hz, 1H), 7.70 (d, J=8.2 Hz, 1H), 7.47 (app.t, J=7.5 Hz, 1H), 7.41 (app.t, J=7.5 Hz, 1H), 7.30 (app.t, J=7.5 Hz, 1H), 7.21 (app.t, J=7.5 Hz, 1H), 5.13 (s, 2H), 1.65 (s, 9H); $^{13}$C NMR (62.5 MHz, DMSO-d$_6$) δ169.9, 139.2, 139.0, 129.9, 127.6, 125.4, 125.3, 124.9, 122.7, 122.4, 122.0, 121.2, 119.7, 118.8, 115.1, 113.6, 111.8, 111.2, 101.9, 53.6, 48.1, 27.8; HRMS (FAB) m/z calc'd for C$_{24}$H$_{22}$N$_3$O (M+H): 368.1762, found 368.1764.

Indolocarbazole 30b. IR (thin film/NaCl) 3487.5 (brs), 3352.0 (brs), 3232.0 (brs), 3022.3 (m), 1579.1 (s), 1571.2 (s), 1517.7 (s), 1462.9 (m), 1399.3 (m), 1262.7 (m), 1237.6 (s), 1142.0 (w), 1016.8 (w), 741.3 (s) cm$^{-1}$; $^1$H NMR (500 MHz, DMSO-d$_6$) δ11.50 (bs, 1H), 11.35 (bs, 1H), 9.28 (d, J=7.9 Hz, 1H), 7.97 (d, J=7.8 Hz, 1H), 7.77 (d, J=8.1 Hz, 1H), 7.73 (d, J=8.1 Hz, 1H), 7.45 (app.t, J=6.9 Hz, 1H), 7.44 (app.t, J=7.1 Hz, 1H), 7.26 (app.t, J=7.1 Hz, 1H), 7.25 (app.t, J=7.1 Hz, 1H), 7.02 (s, 1H), 6.92 (s, 2H), 4.94 (s, 2H), 4.82 (s, 2H), 3.74 (s, 3H), 3.71 (s, 3H); $^{13}$C NMR (62.5 MHz, DMSO-d$_6$) δ 169.2, 148.9, 148.1, 139.1, 139.0, 130.6, 130.0, 127.7, 125.3, 124.9, 124.9, 124.8, 122.6, 122.3, 120.7, 119.9, 119.7, 118.8, 118.2, 115.4, 113.8, 112.3, 112.1, 111.71, 111.1, 55.5, 49.3, 45.4; HRMS (FAB) m/z calc'd for C$_{29}$H$_{24}$N$_3$O$_3$ (M+H): 462.1817, found 462.1813.

Indolocarbazole 30c. IR (thin film/NaCl) 3429.3 (brs), 3351.3 (brs), 2912.4 (m), 1609.7 (s), 1580.3 (s), 1512.0 (s), 1465.5 (s), 1402.1 (w), 1250.61 (s), 1238.4 (s), 1177.3 (m), 1030.8 (w), 748.9 (s) cm$^{-1}$; $^1$H NMR (500 MHz, DMSO-d$_6$) δ11.53 (bs, 1H), 11.37 (bs, 1H), 9.28 (d, J=7.8 Hz, 1H), 7.99 (d, J=7.7 Hz, 1H), 7.78 (d, J=8.1 Hz, 1H), 7.75 (d, J=8.1 Hz, 1H), 7.47 (app.t, J=7.0 Hz, 1H), 7.45 (app.t, J=7.1 Hz, 1H), 7.36 (d, J=8.4 Hz, 2H), 7.28 (app.t, J=7.9 Hz, 1H), 7.26 (app.t, J=7.8 Hz, 1H), 6.94 (d, J=8.5 Hz, 2H), 4.94 (s, 2H), 4.83 (s, 2H), 3.72 (s, 3H); $^{13}$C NMR (62.5 MHz, DMSO-d$_6$) δ 169.2, 158.4, 139.1, 139.0, 130.0, 129.9, 128.9, 127.7, 125.3, 124.9, 124.8, 122.6, 122.2, 120.7, 119.7, 118.8, 118.2, 115.4, 113.9, 113.8, 111.7, 111.1, 54.9, 49.2, 45.0; HRMS (FAB) m/z calc'd for C$_{28}$H$_{22}$N$_3$O$_2$ (M+H): 432.1712, found 432.1699.

(+)-N-3,4-Dimethoxybenzyl-K252a (36). Aglycone 30c (0.22 mmol) and (–)-2,5-dimethoxy sugar (0.87 mmol; 4.0 eq) were refluxed in dry 1,2- dichloroethane (7.5 mL) in the presence of camphorsulfonic acid (0.022 mmol, 0.1 eq) for 48 h. The reaction mixture was allowed to cool to 25° C., diluted with 5.0 mL CH$_2$Cl$_2$, and washed with 5.0 mL 10% NaHCO$_3$ sln. The organic layer was evaporated and purified by preparative tlc (1:60, MeOH:70% CH$_2$Cl$_2$/hexanes, 3 elutions) giving (+)-36 (75.0 mg, 0.120 mmol, 55%) and (+)-37 (34.0 mg, 0.055 mmol, 25%).

Indolocarbazole (+)-36. IR (thin film/NaCl) 3279.7 (brm), 3012.1 (m), 2952.1 (m), 2930.1 (m), 2850.1 (w), 1732.2 (m), 1646.2 (s), 1590.4 (m), 1513.7 (s), 1460.2 (s), 1260.3 (s), 1139.5 (s), 1028.1 (m), 744.5 (s) cm$^{-1}$; $^1$H NMR (500 MHz, DMSO-d$_6$) δ9.26 (d, J=7.9 Hz, 1H), 7.99 (d, J=7.7 Hz, 1H), 7.92 (app.t, J=8.0 Hz, 2H), 7.49 (app.t, J=7.7 Hz, 1H), 7.47 (app.t, J=7.8 Hz, 1H), 7.32 (app.t, J=7.9 Hz, 1H), 7.30 (app.t, J=8.1 Hz, 1H), 7.15 (dd, J=5.2, 6.9 Hz, 1H), 7.02 (s, 1H), 6.94 (d, J=9.0 Hz, 1H), 6.92 (d, J=9.0 Hz, 1H), 6.35 (s, 1H), 5.0 (dd, J=17.8, 25.9 Hz, 2H), 4.84 (dd, J=15.5, 17.5 Hz, 2H), 3.92 (s, 3H), 3.74 (s, 3H), 3.71 (s, 3H), 3.39 (dd, J=7.3, 14.0 Hz, 1H), 2.13 (s, 3H), 2.00 (dd, J=4.7, 14.0 Hz, 1H); $^{13}$C NMR (62.5 MHz, DMSO-d$_6$) δ172.6, 168.6, 148.9, 148.2, 139.8, 136.7, 130.4, 130.0, 128.2, 125.3, 125.3, 124.8, 123.9, 123.8, 122.4, 120.9, 120.2, 119.8, 119.3, 118.9, 115.6, 114.6, 114.2, 112.3, 112.1, 108.8, 99.3, 84.8, 55.5, 52.4, 49.5, 45.4, 42.4, 22.6; HRMS (FAB) m/z calc'd for C$_{36}$H$_{32}$N$_3$O$_7$ (M+H): 618.2240, found 618.2240; [α]Dhu 20 (+)-15° (c=0.1, MeOH).

Indololcarbazole (+)-37. IR (thin film/NaCl) 3462.3 (brm), 3014.0 (m), 2952.3 (m), 2925.1 (m), 2849.7 (m), 1730.8 (s), 1645.0 (m), 1514.7 (m), 1455.6 (m), 1403.9 (m), 1348.5 (m), 1312.6 (m), 1257.2 (s), 1235.0 (s), 1138.1 (s), 1068.8 (m), 1027.3 (m),m 750.3 (s) cm$^{-1}$; $^1$H NMR (500 MHz, DMSO-d$_6$) δ9.54 (d, J=7.9 Hz, 1H), 8.01 (d, J=7.9 Hz, 1H), 7.94 (d, J=8.2 Hz, 1H), 7.89 (d, J=8.5 Hz, 1H), 7.50 (app.t, J=7.5 Hz, 1H), 7.45 (app.t, J=7.5 Hz, 1H), 7.30 (app.t, J=7.5 Hz, 1H), 7.29 (app.t, J=7.6 Hz, 1H), 7.14 (dd, J=5.0, 7.2 Hz, 1H), 7.01 (d, J=0.71 Hz, 1H), 6.92 (app.t, J=8.2 Hz, 1H), 6.92 (dd, J=1.1, 8.4 Hz, 1H), 6.34 (bs, 1H0, 4.97 (dd, J=17.9, 21.3 Hz, 2H), 4.83 (dd, J=15.1, 21.9 Hz, 2H), 3.92 (s, 3H), 3.74 (s, 3H), 3.71 (s, 3H), 3.40 (dd, J=7.5, 14.0 Hz, 1H), 2.14 (s, 3H), (dd, J=4.8, 14.0 Hz, 1H); $^{13}$C NMR (62.5 MHz, DMSO-d$_6$) δ172.6, 168.9, 149.0, 148.2, 139.7, 136.8, 130.4, 126.2, 126.1, 125.4, 125.1, 124.9, 124.3, 122.0, 121.3, 120.2, 119.8, 119.2, 118.7, 116.3, 113.9, 113.8, 112.3, 112.1, 109.4, 99.3, 84.9, 84.8, 55.5, 52.4, 49.0, 45.4, 42.5, 22.8; HRMS (FAB) m/z calc'd for C$_{36}$H$_{32}$N$_3$O$_7$ (M+H): 618.2240, found 618.2240; [α]D$^{20}$ (+)-13° (c=0.1, MeOH).

(+)-K252a, (14). To a stirred solution of (+)-36 (17.0 mg, 0.028 mmol) in CH$_2$Cl$_2$ (1.4 mL) at 25° C. was added thioanisole (0.16 mL, 1.4 mmol, 50 eq) followed by 2,2,2-trifluoroacetic acid (1.4 mL). The solution was stirred for 6 h, at which point 2.0 mL sat. NaHCO$_3$ sln. was added dropwise to neutralize the reaction mixture, the organic layer was separated, evaporated and purified via preparative tlc (1:40, MeOH:50% CH$_2$Cl$_2$/hexanes, 3 elutions) giving (+)-K252a (10.8 mg, 0.023 mmol, 83%).

Preparation of desamido K252a (40) To a suspension of indolo[2,3-a]carbazole (10) (1.0 g, 3.9 mmol) in 1,2-dichloroethane (130 mL) was added furanose 9 (1.8 g, 8.2 mmol) followed by CSA (100 mg, 0.43 mmol). The suspension was heated at reflux for 48 h, following which the reaction was allowed to cool to room temperature and was diluted with CH$_2$Cl$_2$ (100 mL), washed with 10% NaHCO$_3$ (aq.), dried over Na$_2$SO$_4$ and chromatographed on silica gel using 3:1 hexanes:ethyl acetate as eluent to afford indolocarbazole 40 (1.37 g, 85%) as a yellow foam. $^1$H NMR (500 MHz, acetone-d$_6$): δ8.18 (app.t, J=6.6 Hz, 1H), 8.18 (app.t, J=5.4 Hz, 1H), 8.00 (m, 2H), 7.89 (d, J=8.5 Hz, 1H), 7.75 (d, J=8.2 Hz, 1H), 7.44 (td, J=0.9, 7.6 Hz, 1H), 7.38 (td, J=1.0, 7.9 Hz, 1H), 7.26 (app.t, J=6.9 Hz, 1H), 7.25 (app.t, J=7.1 Hz, 1H), 7.10 (dd, J=4.9, 7.3 Hz, 1H), 5.18 (s, 1H), 3.99 (s, 3H), 3.44 (dd, J=7.5, 14.0 Hz, 1H), 2.21 (s, 3H), 2.19 (dd, J=4.9, 14.0 Hz, 1H). $^{13}$C NMR (125 MHz, acetone-d$_6$): δ174.1, 140.8, 138.1, 127.7, 127.0, 125.6, 125.6, 125.5, 125.4, 121.6, 121.5, 121.2, 120.5, 120.4, 120.3, 115.0, 113.1, 112.8, 109.6, 99.9, 86.1, 86.0, 53.3, 43.2, 23.3. IR (thin film/NaCl): 3501.3 (brm), 3047.5 (m), 3006.7 (m), 2950.6 (m), 1729.4 (s), 1640.2 (m), 1568.1 (m), 1441.1 (s), 1305.9 (s), 1230.3 (s), 1128.1 (s), 740.0 (s) cm$^{-1}$. HRMS (EI) m/z Calc'd for $C_{25}H_{20}N_2O_4$: 412.1423. Found: 412.1419.

Preparation of aldehyde 41 To a stirred solution of ester 11 (1.0 g, 2.43 mmol) in THF (24.3 mL), was added LiBH$_4$ (106 mg, 4.85 mmol) at room temperature. After 20 min the solvent was removed in vacuo. To the white residue was added 50 mL 1.0 N HCl on an ice bath. The aqueous phase was extracted with CH$_2$Cl$_2$ (3×50 mL). The combined organic phases were dried with Na$_2$SO$_4$ and chromatographed on silica gel using 1:1 hexanes:ethyl acetate as eluent to afford a diol (815 mg, 87%) as a white solid. $^1$H NMR (500 MHz, acetone-d$_6$): δ8.18 (d, J=7.6 Hz, 1H), 8.15 (d, J=7.8 Hz, 1H), 7.96 (s, 2H), 7.89 (d, J=8.5 Hz, 1H), 7.65 (d, J=8.1 Hz, 1H), 7.42 (app.t, J=7.6 Hz, 1H), 7.36 (app.t, J=8.2 Hz, 1H), 7.25 (app.t, J=7.6 Hz, 1H), 7.23 (app.t, J=7.4 Hz, 1H), 6.91 (J=5.2, 7.4 Hz, 1H), 4.57 (s, 1H), 4.18 (app.t, J=5.9 Hz, 1H), 4.06 (dd, J=5.4, 11.1 Hz, 1H), 3.90 (dd, J=7.1, 11.1 Hz, 1H), 3.30 (dd, J=7.6, 13.8 Hz, 1H), 2.23 (dd, J=5.1, 13.8 Hz, 1H), 2.22 ( s, 3H), $^{13}$C NMR (125 MHz, acetone-d$_6$): δ140.2, 137.4, 127.6, 126.3, 125.4, 125.0, 124.6, 124.6, 120.7, 120.6, 119.9, 119.5, 114.6, 112.2, 112.0, 108.8, 100.1, 84.2, 83.8, 65.5, 40.6, 21.5. IR (thin film/NaCl): 3416.8 (brs), 3052.9 (m), 3010.5 (m), 2955.4 (w), 1732.7 (w), 1640.9 (m), 1568.5 (m), 1492.6 (m), 1459.0 (s), 1441.4 (s), 1309.0 (s), 1233.1 (s), 1031.9 (s), 741.0 (s) cm$^{-1}$. HRMS (EI) m/z Calc'd for $C_{24}H_{20}N_2O_3$: 384.1474. Found: 384.1472. To a stirred solution of the diol (500 mg, 1.3 mmol) in 1:1 benzene:DMSO (8.7 mL) was added pyridinium trifluoroacetate (250 mg, 1.3 mmol) followed by 1,3-cicylohexylcarboiimide (810 mg, 3.9 mmol). The flask was then quickly sealed with a septum, evacuated, and flushed with N$_2$ (3×). The heterogeneous mixture was stirred for 7h until reaction was complete as indicated by TLC. Benzene (15 mL) was added to the mixture and the 1,3-dicyclohexylurea (DCU) precipitate was filtered. The filtrate was washed with H$_2$O (3×20 mL), and the combined aqueous layers were back extracted with CH$_2$Cl$_2$ (3×3 mL). All organic layers were combined, dried with Na$_2$SO$_4$, and evaporated to an oily residue. A minimum amount of acetone (2 mL) was added to precipitate the remaining DCU. Filtration and evaporation to a yellow oil, which was purified by MPLC (3:1 hexanes:ethyl acetate) gave aldehyde 41 (375 mg, 73%, 63% 2 steps) as a yellow powder. $^1$H NMR (500 MHz, CDCl$_3$): δ9.70 (s, 1H), 7.99 (app.t, J=7.3 Hz, 2H), 7.78 (s, 2H), 8.02 (d, J=8.4 Hz, 1H), 7.29 (app.t, J=7.4 Hz, 1H), 7.24 (app.t, J=7.2 Hz, 1H), 7.22 (d, J=8.4 Hz, 1H), 7.17 (app.t, J=7.9 Hz, 1H), 7.15 (app.t, J=7.2 Hz, 1H), 6.59 (dd, J=5.0, 7.4 Hz, 1H), 3.08 (s, 1H), 2.76 (dd, J=7.6, 14.6 Hz, 1H), 1.99 (s, 3H), 1.83 (dd, J=5.0, 14.7 Hz, 1H). $^{13}$C NMR (125 MHz, CDCl$_3$): δ199.4, 139.3, 136.9, 126.3, 126.3, 125.1, 124.7, 124.1, 121.2, 121.1, 120.8, 120.3, 120.3, 119.9, 113.1, 112.9, 122.2, 108.0, 97.7, 87.7, 84.0, 89.7, 23.0. IR (thin film/NaCl): 3486.7 (brm), 3054.6 (m), 3007.7 (m), 2945.8 (m), 2843.4 (w), 1723.9 (m), 1641.8 (m), 1568.6 (m), 1458.7 (m), 1441.1 (s), 1309.2 (s), 1232.5 (s), 1128.8 (m), 1004.2 (m), 741.7 (s) cm$^{-1}$. HRMS (EI) m/z Calc'd for $C_{24}H_{18}N_2O_3$: 382.1317. Found: 382.1319.

Preparation of hydroxy ketone 43 To a suspension of aldehyde 12 (75 mg, 0.196 mmol) in Et$_2$O (5.0 mL) was added BF$_3$·OEt$_2$ (27 μL, 0.216 mmol) and the mixture stirred vigorously for 6h. CH$_2$Cl$_2$ (25 mL) was added to solubilize the suspension and the resulting solution was evaporated onto SiO$_2$ (100 mg) and chromatographed using 2:1 hexanes:ethyl acetate as eluent to provide ketone 43 (47 mg, 60%) as a white powder. $^1$H NMR (500 MHz, CDCl$_3$): δ8.15 (d, J=7.7 Hz, 1H), 8.10 (d, J=7.7 Hz, 1H), 7.97 (d, J=8.5 Hz, 1H), 7.92 (d, J=8.2 Hz, 1H), 7.90 (d, J=8.2 Hz, 1H), 7.43 (app.t, J=7.7 Hz, 1H), 7.39 (app.t, J=7.8 Hz, 1H), 7.32 (app.t, J=7.4 Hz, 1H), 7.28 (app.t, J=7.5 Hz, 1H), 7.25 (d, J=8.1 Hz, 1H), 7.06 (d, J=7.3 Hz, 1H), 4.89 (d, J=6.0 Hz, 1H), 3.55 (dd, J=7.5, 14.3 Hz, 1H), 3.49 (d, J=6.5 Hz, 1H), 2.99 (d, J=14.4 Hz, 1H), 2.54 (s, 3H). $^{13}$C NMR (125 MHz, CDCl$_3$): δ199.8, 140.2, 136.3, 126.4, 125.7, 125.4, 125.1, 124.8, 124.6, 121.4, 120.8, 120.4, 120.2, 119.8, 115.2, 112.7, 112.4, 112.1, 107.9, 100.3, 84.03, 81.6, 44.7, 29.5. IR (thin film/NaCl): 3328.6 (brm), 3048.0 (w), 2923.7 (m), 2852.1 (w), 1731.4 (s), 1637.4 (m), 1441.5 (s), 1395.3 (m), 1312.0 (s), 1130.1 (m), 740.8 (s) cm$^{-1}$. HRMS (EI) m/z Calc'd for $C_{24}H_{18}N_2O_3$: 382.1317. Found: 382.1315.

Preparation of methoxy ketone 44 Montmorillonite Clay K-10 (1.2 g) was premixed with trimethylorthoformate (1.78 mL, 16.3 mmol) and immediately transfer to a stirred solution of aldehyde 12 (414 mg, 1.1 mmol) in CHCl$_3$ (11 mL) aided by an additional 3 mL CHCl$_3$. The reaction was monitored by TLC (3:1 hexanes:ethyl acetate) and after approximately 0.5 h formation of the dimethyl acetal 16 was complete. The reaction mixture was filtered, and the filtrate evaporated in vacuo. The residue was dissolved in diethyl ether (110 mL) under an inert atmosphere, followed by addition of BF$_3$·OEt$_2$ (2.85 mL, 23.1 mmol). The mixture was stirred for 4 d at 25° C., following which triethyl amine (6.1 mL) and CH$_2$Cl$_2$ (100 mL) were added, the solution was evaporated under reduced pressure and chromatographed on silica gel using 2:1 hexanes:ethyl acetate as eluent to afford methoxy ketone 44 (214 mg, 50%) as a yellow foam. $^1$H NMR (500 MHz, DMSO-d$_6$): δ8.21 (d, J=7.7 Hz, 1H), 3.16 (d, J=7.8 Hz, 1H), 7.97 (d, J=8.2 Hz, 1H), 7.95 (d, J=8.2 Hz, 1H), 7.88 (d, J=8.6 Hz, 1H), 7.68 (d, J=8.1 Hz, 1H), 7.46 (td, J=1.0, 7.4 Hz, 1H), 7.37 (td, J=1.1, 7.7 Hz, 1H), 7.36 (d, J=7.2 Hz, 1H), 7.30 (app.t, J=7.6 Hz, 1H), 7.23 (app.t, J=7.4 Hz, 1H), 5.02 (s, 1H), 3.94 (dd, J=7.2, 13.7 Hz, 1H), 3.39 (s, 3H), 2.62 (d, J=13.9 Hz, 1H), 2.52 (s, 3H). $^{13}$C NMR (125 MHz, DMSO-d$_6$): δ199.8, 139.4, 135.7, 125.0, 124.8, 124.5, 124.1, 124.0, 120.0, 119.8, 119.4, 119.2, 114.9, 112.1, 111.3, 109.2, 99.0, 88.2, 84.4, 58.9, 45.4, 29.2. IR (thin film/NaCl): 3046.6 (brm), 3003.8 (brw), 2927.9 (m), 2835.6 (m), 1736.6 (s), 1640.5 (m), 1565.8 (m), 1492.7 (m), 1442.9 (s), 1311.5 (s), 114.3 (m), 1126.1 (s), 740.2 (s) cm$^{-1}$. HRMS (EI) m/z Calc'd for $C_{25}H_{20}N_2O_3$: 396.1474. Found: 396.1474.

Preparation of desamido TAN-1030a (47) A suspension of ketone 15 (30 mg, 0.08 mmol), hydroxylamine hydrochloride (17 mg, 0.24 mmol), and NaOAc (20 mg, 0.24 mmol) in 50% aqueous EtOH (2.0 mL) was heated gently to reflux for 30 min. Following cooling to room temperature, sovent was removed in vacuo, and the residue purified by MPLC (2:1 hexanes:ethyl acetate) to provide oxime 47 (26 mg, 85%) as a yellow powder. $^1$H NMR (500 MHz, DMSO-d$_6$): δ10.43 (s, 1H), 8.17 (d, J=7.8 Hz, 1H), 8.13 (d, J=7.4 Hz, 1H), 7.91 (d, J=8.4 Hz, 1H), 7.89 (d, J=8.4 Hz, 1H), 7.88 (d, J=8.4 Hz, 1H), 7.67 (d, J=8.2 Hz, 1H), 7.44 (app.t, J=7.6 Hz, 1H), 7.34 (app.t, J=7.7 Hz, 1H), 7.27 (app.t, J=7.5 Hz, 1H), 7.20 (app.t, J=7.4 Hz, 1H), 6.98 (d, J=5.5 Hz, 1H), 4.70 (s, 1H), 3.61 (d, J=14.1 Hz, 1H), 3.42 (s, 3H), 2.97 (dd, J=5.7, 14.3 Hz, 1H), 2.42 (s, 3H). $^{13}$C NMR (125 MHz, DMSO-d$_6$): δ 145.3, 139.3, 135.9, 126.0, 125.1, 124.9, 124.6, 124.2, 124.0, 120.0, 119.6, 119.4, 119.1, 119.1, 115.0, 111.8, 111.0, 109.1, 95.9, 83.7, 82.2, 58.3, 29.7, 28.4. IR (thin film/NaCl): 3249.5 (brm), 2918.3 (s), 2848.4 (s), 1728.1 (m), 1640.2 (m), 1443.1 (s), 1398.1 (m), 1312.0 (m), 1124.5 (s), 740.7 (s) cm$^{-1}$. HRMS (EI) m/z Calc'd for C$_{25}$H$_{21}$N$_3$O$_3$: 411.1583. Found: 411.1582.

Preparation of desamido RK-286c (46) To a stirred solution of keton 15 (12 mg, 0.03 mmol) in 1:1 MeOH: CH$_2$Cl$_2$ (1.0 mL) was added NaBH$_4$ (3 mg, 0.08 mmol) at room temperature. After 5 minutes solvent was removed under reduced pressure. To the white residue was added 1 mL 1.0 N HCl on an ice bath. The mixture was stirred for 15 min at 25° C. and extracted with CH$_2$Cl$_2$ (3×1 mL). The combined organic phase were dried with Na$_2$SO$_4$ and chromatographed on silica gel using 2:1 hexanes:ethyl acetate as eluent to afford alcohol 46 (12 mg, 95%) as a white solid. $^1$H NMR (500 MHz, CDCl$_3$): δ8.14 (d, J=7.7 Hz, 1H), 8.11 (d, J=7.7 Hz, 1H), 7.90 ( d, J=8.2 Hz, 1H), 7.85 (d, J=8.2 Hz, 1H), 7.81 (d, J=8.5 Hz, 1H), 7.39 (td, J=1.0, 8.1 Hz, 1H), 7.35 (ddd, J=14, 7.1, 8.4 Hz, 1H) 7.25 (m, 3H), 6.54 (d, J=5.6 Hz, 1H), 4.34 (m, 1H), 3.66 (d, J=3.0 Hz, 1H), 3.53 (s, 3H), 2.71.dd (3.5, J=14.9 Hz, 1H), 2.45 (m, 1H), 2.30 (s, 3H), 1.66 (bs, 1H), $^{13}$C NMR (125 MHz, CDCl$_3$): δ139.6, 136.6, 128.3, 127.2, 126.5, 126.2, 124.8, 124.4, 123.9, 120.5, 120.3, 119.6, 119.3, 114.9, 112.1, 110.9, 107.6, 90.6, 83.1, 79.7, 60.5, 57.4, 33.7, 29.9, IR (thin film/NaCl): 3528.3 (brm), 3048.1 (m), 3000.2 (m), 2928.4 (m), 1643.7 (m), 1564.8 (m), 1498.8 (m), 1445.1 (s), 1344.4 (m), 1311.6 (s), 1231.2 (s), 1109.5 (brs) cm$^{-1}$. HRMS (EI) m/z Calc'd for C$_{25}$H$_{22}$N$_2$O$_3$: 398.1630. Found: 398.1633.

Preparation of aldehyde (+)-50 To a stirred solution of ester (+)-36 (150 mg, 0.243mmol) in THF (2.5 mL) was added LiBH$_4$ (12 mg, 0.535 mmol) at room temperature. After 20 min solvent was removed in vacuo. To the white residue, 10.0 mL 1.0 N HCl was added on an ice bath. The aqueous phase was extracted with CH$_2$Cl$_2$ (3×20 mL). The combined organic phases were dried with Na$_2$SO$_4$ and chromatographed on silica gel using 1:1 hexanes:ethyl acetate as eluent to afford a diol (124 mg, 89%) as a white solid. $^1$H NMR (500 MHz, DMSO-d$_6$): δ9.25 (d, J=7.9 Hz, 1H), 7.97 (d, J=7.2 Hz, 1H), 7.96 (d, J=8.1 Hz, 1H), 7.78 (d, J=8.3 Hz, 1H), 7.48 (app.t, J=7.6 Hz, 1H), 7.43 (app.t, J=7.8 Hz, 1H), 7.29 (app.t, J=7.1 Hz, 1H), 7.28 (app.t, J=7.2 Hz, 1H), 7.02 (s, 1H), 7.96 (dd, J=5.2, 7.2 Hz, 1H), 6.94 (s, 2H), 5.38 (s, 1H), 5.06 (t, J=5.6 Hz, 1H), 5.02 (d, J=17.7 Hz, 1H), 4.95 (d, J=17.6 Hz, 1H), 4.85 (d, J=15.9 Hz, 1H), 4.85 (d, J=15.7 Hz, 1H), 3.85–3.81 (m, 2H), 3.75 (s, 3H), 3.72 (s, 3H), 3.14 (dd, J=7.6, 13.7 Hz, 1H), 2.15 (s, 3H), 1.94 (dd, J=4.8, 13.7 Hz, 1H). $^{13}$C NMR (125 MHz, DMSO-d$_6$): δ168.9, 148.9, 148.1, 140.0, 136.7, 130.5, 130.2, 128.7, 125.4, 125.3, 124.6, 124.3, 123.8, 122.4, 120.9, 120.0, 119.8, 119.2, 118.5, 115.2, 114.9, 114.0, 112.1, 111.8, 108.7, 100.2, 83.5, 64.7, 55.5, 55.5, 49.6, 45.4, 40.2, 40.1, 21.3. IR (thin film/NaCl): 3343.8 (brm), 3001.5 (w), 2950.7 (m), 2926.1 (m), 1647.4 (s), 1588.0 (m), 1514.4 (m), 1459.7 (s), 1422.2 (m), 1399.6 (m), 1312.4 (m), 1138.0 (s), 744.7 (s) cm$^{-1}$. [α]D$^{25}$+112° (c=0.1, MeOH). To a stirred solution of the diol (395 mg, 067 mmol) in 1:1 benzene:DMSO (4.6 mL) was added pyridinium trifluoroacetate (130 mg, 0.67 mmol) followed by 1,3-dicyclohexylcarbodiimide (415 mg, 2.01 mmol). The flask was then quickly sealed with a septum, evacuated, and flushed with N$_2$ (3×). The heterogeneous mixture was stirred for 9 h until reaction was complete as indicated by TLC. Benzen (5.0 mL) was added to the mixture and the 1,3-dicyclohexylurea (DCU) precipitate was filtered. The filtrate was wahsed with H$_2$O (3×5.0 mL), and the combined aqueous layers were back extracted with CH$_2$Cl$_2$ (3×10.0 mL). All organic layers were combined, dried with Na$_2$SO$_4$, and evaporated to an oily residue. A minimum amount of acetone (2 mL) was added to precipitate the remaining DCU. Filtration and evaporation to a yellow oil, which was purified by MPLC (2:1→1:1 hexanes:ethyl acetate) gave aldehyde (+)-50 (280 mg, 71%, 63% 2 steps) as a yellow powder. $^1$H NMR (500 MHz, DMSO-d$_6$): δ10.07 (s, 1H), 9.31 (d, J=7.9 Hz, 1H), 8.02 (d, J=8.5 Hz, 1H), 7.99 (d, J=7.7 Hz, 1H), 7.87 (d, J=8.2 Hz, 1H), 7.50 (app.t, J=8.1 Hz, 1H), 7.47 (app.t, J=8.2 Hz, 1H), 7.32 (app.t, J=8.1 Hz, 1H), 7.17 (dd, J=7.2, 4.8 Hz, 1H), 7.04 (s, 1H), 6.94 (d, J=9.6 Hz, 1H), 6.93 (d, J=8.1 Hz, 1H), 6.57 (bs, 1H), 5.02 (d, J=17.6 Hz, 1H), 4.98 (d, J=17.7 Hz, 1H), 4.87 (d, J=15.2 Hz, 1H), 4.83 (d, J=15.2 Hz, 1H), 3.76 (s, 3H), 3.73 (s, 3H), 3.24 (dd, J=7.6, 14.0 Hz, 1H), 2.22 (s, 3H), 2.00 (dd, J=4.5, 14.0 Hz, 1H). $^{13}$C NMR (125 MHz, DMSO-d$_6$): δ202.2, 168.7, 148.9, 148.1, 139.9, 136.9, 130.4, 130.2, 128.2, 125.2, 125.5, 125.1, 123.9, 123.9, 122.5, 121.1, 120.4, 119.9, 119.6, 119.1, 115.8, 114.6, 114.4, 112.1, 111.8, 109.0, 98.7, 86.8, 84.3, 55.5, 55.5, 49.6, 45.5, 39.4, 22.7. IR (thin film/NaCl): 3253.9 (brm), 3010.7 (m), 2953.6 (m), 2934.0 (m), 2833.9 (s), 1734.0 (s), 1646.2 (s), 1614.7 (w), 1589.9 (m), 1514.1 (m), 1399.1 (s), 1275.7 (m), 1138.4 (s), 1024.8 (m), 745.1 (s) cm$^{-1}$. [α]D$^{25}$30 48° (c=0.1, MeOH).

Preparation of hydroxy ketone (+)-51 To a suspension of aldehyde (+)-50 (100 mg, 0.170 mmol) in Et$_2$O (17.0 mL) was added BF$_3$·OEt$_2$ (23 μL, 0.187 mmol) and the mixture stirred vigorously for 12 h at 25–30° C., when again was treated with BF$_3$·OEt$_2$ (23 μL, 0.187 mmol) and stirred for an additional 12 h at the same temperature. The reaction mixture was filtered to provide ketone (+)-51 (85 mg, 85%) as a white powder. $^1$H NMR (500 MHz, DMSO-d$_6$, 310 K): δ9.35 (d, J=7.9 Hz, 1H), 8.06 (d, J=8.6 Hz, 1H), 7.92 (d, J=7.7 Hz, 1H), 7.72 (d, J=8.2 Hz, 1H), 7.53 (app.t, J=7.6 Hz, 1H), 7.43 (app.t, J=8.1 Hz, 1H), 7.40 (d, J=6.6 Hz, 1H), 7.35 (app.t, J=7.5 Hz, 1H), 7.29 (app.t, J=7.4 Hz, 1H), 7.02 (s, 1H), 6.93 (s, 2H), 6.12 (d, J=5.1 Hz, 1H), 5.23 (d, J=4.5 Hz, 1H), 4.96 (s, 2H), 4.85 (d, J=15.1 Hz, 1H), 4.81 (d, J=15.1 Hz, 1H), 3.97 (dd, J=6.7, 14.1 Hz, 1H), 3.75 (s, 3H), 3.72 (s, 3H), 2.66 (d, J=14.1 Hz, 1H), 2.54 (s, 3H). $^{13}$C NMR (500 MHz, DMSO-d$_6$): δ 201.1, 168.6, 148.9, 148.1, 140.3, 136.0, 130.4, 129.8, 126.9, 125.6, 125.5, 124.9, 124.0, 123.6, 122.8, 120.7, 120.4, 119.9, 119.9, 118.8, 115.9, 115.1, 114.3, 112.1, 111.8, 109.2, 100.5, 84.4, 80.0, 55.5, 55.5, 49.6, 45.4, 44.9, 29.4. IR (thin film/NaCl): 3300.0 (brs), 2999.5 (brm), 2848.6 (m), 1728.9 (m), 1665.5 (s), 1503.3 (m), 1451.2 (s), 1406.8 (m), 1132.8 (s), 1021.9 (m), 750.6 (s), cm$^{-1}$. [α]D$^{25}$+83° (c=0.1, DMSO).

Preparation of Ester (+)-35 To a solution of ketone (+)-51 (10 mg, 0.017 mmol) in 1:1 MeOH/CH$_2$Cl$_2$ (1.0 mL) was added Copper (I) chloride (30 mg, 0.30 mmol), and the mixture warmed to reflux for 15 min. Solvent was removed in vacuo and the resulting residue subjected to silica gel chromatography (1:1, hexanes:ethyl acetate) to afford (+)-36 (10 mg, 95%) as a colorless solid.

Preparation of diol (+)-53 To a stirred solution of ketone (+)-51 (85 mg, 0.15 mmol) in 1:1:2 MeOH:CH$_2$Cl$_2$:CHCl$_3$ (20.0 mL), NaBH$_4$ (20 mg, 0.53 mmol) was added at room temperature. After 5 minutes solvent was removed under reduced pressure. To the white residue, 10 mL 1.0 N HCl was added on an ice bath. The mixture was stirred for 15 min at 25° C. and extracted with CH$_2$Cl$_2$ (3×20 mL). The combined organic phases were dried with Na$_2$SO$_4$ and chromatographed on silica gel using 1:1 hexanes:ethyl acetate as eluent to afford alcohol (+)-53 (81 mg, 95%) as a white solid. $^1$H NMR (500 MHz, acetone-d$_6$): δ9.53 (d, J=7.9 Hz, 1H), 8.11 (d, J=8.5 Hz, 1H), 7.88 (d, J=7.7 Hz, 1H), 7.51 (d, J=8.2 Hz, 1H), 7.46 (app.t, J=7.2 Hz, 1H), 7.36 (app.t, J=7.9 Hz, 1H), 7.29 (app.t, J=7.4 Hz, 1H), 7.22 (app.t, J=7.4 Hz, 1H), 7.08 (s, 1H), 6.98 (d, J=8.3 Hz, 1H), 6.91 (d, J=8.2 Hz, 1H), 6.76 (d, J=5.1 Hz, 1H), 4.95 (d, J=17.1 Hz, 1H), 4.90 (d, J=71.1 Hz, 1H), 4.89 (d, J=15.2 Hz, 1H), 4.85 (d, J=15.2 Hz, 1H), 4.24 (d, J=0.85 Hz, 1H), 4.23 (bs, 1H), 4.14 (d, J=8.6 Hz, 1H), 3.77 (s, 3H), 3.76 (s, 3H), 3.64 (bs, 1H), 2.76 (d, J=15.1 Hz, 1H), 2.65 (d, J=15.1 Hz, 1H), 2.35 (s, 3H), $^{13}$C NMR (125 MHz, acetone-d$_6$): δ170.4, 150.6, 149.7, 141.2, 137.7, 132.0, 130.7, 130.4, 127.6, 127.1, 125.8, 125.3, 125.0, 124.3, 121.5, 121.0, 120.6, 120.0, 119.8, 116.6, 116.0, 115.0, 112.8, 108.9, 93.3, 80.6, 74.7, 65.4, 56.1, 50.4, 46.6, 35.4, 30.4. IR (thin film/NaCl): 3355.5 (brm), 2922.9 (m), 2847.8 (m), 1654.5 (s), 1501.5 (w), 1449.3 (s), 1254.5 (s), 1136.8 (s), 1025.7 (m), 747.1 (s) cm$^{-1}$. [α]D$^{25}$+37° (c=0.1, MeOH). Preparation of methyl ether (+)-54 To a stirred suspension of NaH (14 mg, 0.58 mmol) in THF (1.0 mL) was added a solution of alcohol (+)-53 (81 mg, 0.138 mmol) in THF (7 mL). The resulting mixture was stirred for 10 min with the visible evolution of gas, and for an additional 15 min thereafter. Addition of MeI (9.5 μL, 0.15 mmol) produced a single product by TLC (2.5:1 hexanes:acetone). After approximately 50 min the reaction was quenched by addition of 1.0 mL 1.0N HCl followed by 2.0 mL H$_2$O. Extraction of the solution with CH$_2$Cl$_2$ (3×10 mL), drying over Na$_2$SO$_4$ and evaporation to a residue which could be purified by MPLC (2.5:1 hexanes: acetone) provided methyl ester (+)-54 (67 mg, 80%) as a yellow foam. $^1$H NMR (500 MHz, CDCl$_3$): δ9.54 (d, J=7.9 Hz, 1H), 7.90 (d, J=8.5 Hz, 1H), 7.81 (d, J=7.7 Hz, 1H), 7.48 (app.t, J=7.6 Hz, 1H), 7.41 (app.t, J=7.2 Hz, 1H), 7.38 (app.t, J=7.2 Hz, 1H), 7.28 (m, 2H), 6.97 (d, J=8.2 Hz, 1H), 6.95 (s, 1H), 6.86 (d, J=8.1 Hz, 1H), 6.60 (d, J=5.8 Hz, 1H), 4.96 (d, J=15.0 Hz, 1H), 4.89 (d, J=15.0 Hz, 1H), 4.84 (d, J=16.7 Hz, 1H), 4.79 (d, J=16.6 Hz, 1H), 4.38 (d, J=2.6 Hz, 1H), 3.88 (s, 3H), 3.85 (s, 3H), 3.71 (d, J=2.6 Hz, 1H), 3.57 (s, 3H), 2.76 (dd, J=3.1, 15.1 Hz, 1H), 2.50 (bd, J=14.7 Hz, 1H), 2.3 (s, 3H). $^{13}$H NMR (125 MHz, CDCl$_3$, 315 K): δ170.3, 149.6, 148.7, 140.1, 136.8, 130.8, 129.4, 127.0, 126.4, 125.3, 124.8, 124.3, 123.7, 120.7, 120.4, 120.2, 120.0, 119.6, 116.0, 115.5, 114.5, 111.6, 111.5, 107.1, 90.7, 83.2, 79.5, 60.6, 57.4, 56.1, 56.0, 49.9, 46.5, 38.6, 30.1. IR (thin film/NaCl): 3423.7 (brm), 2923.2 (s), 2848.1 (m), 2636.2 (m), 1647.2 (s), 1514.3 (m), 1462.9 (s), 1258.0 (m), 1235.3 (m), 1136.9 (m), 1026.9 (w), 743.3 (s) cm$^{-1}$. [α]D$^{25}$+48° (c=0.1, MeOH).

Preparation of (+)-RK-286c (50) To a stirred solution of ether (+)-54 (10 mg, 0.017 mmol) in anisole or thioanisole (80 μL, =50 equiv) was added TFA (0.5 mL). The reaction was monitored by TLC, and after 24 h had proceeded to completion, whereupon 1.0 mL H$_2$O was added, followed by extraction with CH$_2$Cl$_2$ (3×5 mL). Combined organic layers were washed with saturated aqueous NaHCO$_3$ (5 mL), dried over Na$_2$SO$_4$, and evaporated to a residue, which was purified by preparative TLC (5% MeOH:CH$_2$Cl$_2$) to provide (+)-RK-286c (50, 6 mg, 75%). $^1$H NMR (500 MHz, DMSO-d$_6$): δ9.27 (d, J=7.9 Hz, 1H), 8.47 (bs, 1H), 7.99 (d, J=8.5 Hz, 1H), 7.94 (d, J=7.7 Hz, 1H), 7.59 (d, J=8.2 Hz, 1H), 7.45 (app.t, J=7.4 Hz, 1H), 7.40 (app.t, J=7.5 Hz, 1H), 7.26 (app.t, J=7.5 Hz, 1H), 6.78 (d, J=5.3 Hz, 1H), 4.95 (d, J=17.6 Hz, 1H), 4.89 (d, J=17.7 Hz, 1H), 4.25 (bs, 1H), 4.17 (bs, 1H), 3.83 (d, J=2.7 Hz, 1H), 3.41 (s, 3H), 2.60 (ddd, J=3.2, 5.6, 14.8 Hz, 1H), 2.41 (dd, J=3.3, 14.8 Hz, 1H), 2.31 (s, 3H). $^{13}$C NMR (125 MHz, DMSO-d$_6$): δ139.7, 136.1, 129.5, 125.5, 124.7, 124.1, 123.9, 122.6, 120.6, 119.5, 118.9, 118.6, 115.7, 108.6, 90.9, 82.3, 79.5, 58.8, 56.4, 45.3, 33.9, 29.9. IR (thin film/NaCl): 3354.0 (brm), 2920.4 (s), 2851.6 (m), 1677.2 (s), 1636.0 (m), 1585.3 (m), 1456.2 (s), 1352.8 (s), 1318.7 (s), 1231.7 (m), 1117.8 (m), 743.8 (s) cm$^{-1}$. [α]D$^{25}$+41.1° (c=0.18, EtOAc); natural RK-286c [α]D$^2$+45.3° (c=0.22, EtOAc).

Preparation of Diol (+)-55 To a stirred solution of ether (+)-54 (112 mg, 0.186 mmol) in CDCl$_3$ (2.0 mL) was added Martin's sulfurane (187 mg, 0.28 mmol). The reaction rapidly proceeded to a less polar product as monitored by TLC, and after 20 min was complete. Solvent was evaporated and the residue subjected to silica gel chromatography (2:1 hexanes:ethyl acetate) to provide an olefin (96 mg, 88%) as a white solid. $^1$H NMR (500 MHz, DMSO-d$_6$, 315 K): δ9.31 (d, J=7.9 Hz, 1H), 8.11 (d, J=8.6 Hz, 1H), 7.91 (d, J=7.7 Hz, 1H), 7.86 (d, J=8.2 Hz, 1H), 7.50 (td, J=1.0, 7.34 Hz, 1H), 7.43 (app.t, J=7.8 Hz, 1H), 7.31 (app.t, J=7.0 Hz, 1H), 7.28 (app.t, J=7.1 Hz, 1H), 7.13 (d, J=1.9 Hz, 1H), 7.02 (s, 1H), 6.93 (d, J=8.6 Hz, 1H), 6.92 (d, J=8.6 Hz, 1H), 6.09 (d, J=10.4 Hz, 1H), 5.77 (dt, J=2.3, 10.4 Hz, 1H), 4.95 (s, 2H), 4.85 (d, J=15.1 Hz, 1H), 4.81 (d, J=15.1 Hz, 1H), 4.48 (d, J=1.4 Hz, 1H), 3.74 (s, 3H), 3.71 (s, 3H), 3.57 (s, 3H), 2.20 (s, 3H). $^{13}$C NMR (125 MHz, acetone-d$_6$): δ169.9, 150.5, 149.7, 141.3, 137.4, 131.8, 131.2, 130.5, 127.7, 127.1, 126.4, 126.2, 125.5, 125.3, 124.3, 121.5, 121.2, 121.1, 120.5, 120.4, 118.0, 117.1, 115.9, 112.8, 112.8, 109.1, 91.5, 80.8, 78.8, 57.7, 56.0, 56.0, 50.5, 46.5, 28.0. IR (thin film/NaCl): 2920.5 (s), 2851.5 (s), 1709.8 (m), 1674.3 (s), 1589.0 (m), 1513.7 (m), 1457.5 (s), 1222.9 (m), 1026.6 (m), 745.3 (m) cm$^{-1}$·[α]D$^{25}$+36° (c=0.1, MeOH). To a stirred solution of 4-methylmorpholine N-oxide (6 mg, 0.05 mmol) and OsO$_4$ (0.06 mL of a 2.5% solution in t-BuOH, 0.05 mmol) in 4:1 acetone:H$_2$O (2 mL) was added solution of the olefin (25 mg, 0.043 mmol) in acetone (1 mL). The reaction was monitored by TLC, and after 16 h had proceeded to completion, whereupon 100 mg NaHSO$_3$ was added in 1.0 mL H$_2$O, and the black solution was stirred for 20 min and filtered, followed by extraction with CH$_2$Cl$_2$ (3×15 mL). Combined organic layers were dried over Na$_2$SO$_4$, and evaporated to a residue, which was purified by MPLC (1:1 hexanes:ethyl acetate) to provide diol (+)-55 (23 mg, 84%) as a white powder. $^1$H NMR (500 MHz, DMSO-d$_6$): δ9.86 (d, J=7.9 Hz, 1H), 7.95 (d, J=8.6 Hz, 1H), 7.94 (d, J=7.6 Hz, 1H), 7.64 (d, J=8.1 Hz, 1H), 7.55 (app.t, J=7.6 Hz, 1H), 7.45 (app.t, J=7.7 Hz, 1H), 7.35 (app.t, J=7.5 Hz, 1H), 7.29 (app.t, J=7.5 Hz, 1H), 7.02 (s, 1H), 6.94 (s, 2H), 6.59 (d, J=1.6 Hz, 1H), 6.13 (d, J=3.8 Hz, 1H), 5.07 (d, J=6.0 Hz, 1H), 4.99 (d, J=17.8 Hz, 1H), 4.95 (d, J=17.8 Hz, 1H), 4.83 (s, 2H), 4.12 (d, J=10.1 Hz, 1H), 4.12 (dd, J=2.3, 3.8 Hz, 1H), 3.74 (s, 3H), 3.72 (s, 3H), 3.62 (s, 3H), 3.55 (ddd, J=2.3, 6.1, 10.1 Hz, 1H), 2.37 (s, 3H). $^{13}$C NMR (125 MHz, DMSO-d$_6$): δ168.8, 148.9, 148.1, 140.3, 136.5, 130.4, 129.9, 127.8, 125.7, 125.0, 124.7, 123.5, 122.7, 120.8, 120.2, 119.9, 119.9, 118.7, 115.5, 114.8, 114.1, 112.0, 111.7, 108.8, 95.6, 87.3, 83.1, 71.7, 65.6, 61.6, 55.5, 55.5, 49.6, 45.5, 29.0. IR (thin film/NaCl): 3411.2 (brm), 2929.3 (m), 2849.4 (w), 2656.3 (m), 1590.0 (m), 1514.0 (m), 1461.2 (s), 1350.9 (m), 1273.6 (s), 1127.1 (s), 1025.0 (m), 743.3 (s) cm$^{-1}$. [α]D$^{25}$+17° (c=0.1, MeOH).

Preparation of (+)-MLR-52 (51) To a stirred solution of diol (+)-55 (10 mg, 0.016 mmol) in anisole or thioanisole (80 μL, =50 eqiv) was added TFA (0.5 mL). The reaction was monitored by TLC, and after 16 h had proceeded to completion, whereupon 1.0 mL H$_2$O was added, followed by extraction with CH$_2$Cl$_2$ (3×5 mL). Combined organic layers were washed with saturated aqueous NaHCO$_3$ (5 mL), dried over Na$_2$SO$_4$, and evaporated to a residue, which was purified by preparative TLC (5% MeOH:CH$_2$Cl$_2$) to provide (+)-MLR-52 (51, 6 mg, 77%). $^1$H NMR (500 MHz, DMSO-d$_6$): δ9.31 (d, J=7.9 Hz, 1H), 8.61 (bs, 1H), 7.99 (d, J=7.7 Hz, 1H), 7.96 (d, J=8.7 Hz, 1H), 7.62 (d, J=8.2 Hz, 1H), 7.53 (app.t, J=7.5 Hz, 1H), 7.45 (td, J=0.8, 7.7 Hz, 1H), 7.32 (app.t, J=7.4 Hz, 1H), 7.32 (app.t, J=7.4 Hz, 1H), 6.58 (d, J=1.6 Hz, 1H), 6.12 (d, J=4.0 Hz, 1H), 5.06 (d, J=5.9 Hz, 1H), 4.99 (d, J=17.6 Hz, 1H), 4.95 (d, J=17.5 Hz, 1H), 4.13 (d, J=10.3 Hz, 1H), 4.12 (dd, J=1.6, 2.6 Hz, 1H), 3.62 (s, 3H), 3.56 (ddd, J=2.6, 6.2, 10.3 Hz, 1H). $^{13}$C NMR (125 MHz, DMSO-d$_6$): δ171.8, 140.2, 132.6, 127.8, 125.8, 125.5, 124.8, 124.6, 123.6, 122.7, 120.9, 120.1, 119.7, 119.3, 115.4, 114.9, 114.3, 108.7, 95.6, 87.2, 88.1, 71.7, 65.6, 61.6, 45.4, 29.0. IR (thin film/NaCl): 3348.5 (brm), 2922.9 (s), 2851.9 (m), 1638.2 (s), 1586.6 (m), 1455.5 (s), 1373.5 (m), 1336.6 (m), 1320.8 (m), 1275.0 (m), 1224.7 (m), 1200.3 (w), 1119.5 (s), 740.8 (s), cm$^{-1}$. [α]D$^{25}$+65° (c=0.1, MeOH): natural MLR-52 [α]D+68° (c=0.093, MeOH).

Preparation of oxime (−-56 A suspension of ketone (+)-51 (100 mg, 0.17 mmol), hydroxylamine hydrochloride (165 mg, 2.38 mmol), and NaOAc (167 mg, 2.04 mmol) in 80% aqueous EtOH (35.0 mL) was heated gently to reflux for 30 min. Following cooling to room temperature, sovent was removed in vacuo, and the residue purified by MPLC (1:1 hexanes:ethyl acetate) to provide oxime (−)-56 (98 mg, 95%) as a yellow powder. $^1$H NMR (500 MHz, DMSO-d$_6$): δ10.3 (s, 1H), 9.34 (d, J=7.9 Hz, 1H), 8.08 (d, J=8.6 Hz, 1H), 7.90 (d, J=7.6 Hz, 1H), 7.71 (d, J=8.3 Hz, 1H), 7.51 (app.t, J=7.6 Hz, 1H), 7.42 (app.t, J=7.9 Hz, 1H), 7.32 (app.t, J=7.7 Hz, 1H), 7.28 (app.t, J=7.4 Hz, 1H), 7.04 (d, J=6.3 Hz, 1H), 7.03 (s, 1H), 6.95 (d, J=8.4 Hz, 1H), 6.93 (d, J=8.2 Hz, 1H), 5.56 (m, 2H), 4.97 (d, J=18.1 Hz, 1H), 4.93 (d, J=16.9 Hz, 1H), 4.85 (d, J=15.0 Hz, 1H), 4.45 (d, J=15.0 Hz, 1H), 3.75 (s, 3H), 3.72 (s, 3H), 3.61 (d, J=13.9 Hz, 1H), 3.01 (dd, J=5.8, 14.3 Hz, 1H), 2.46 (s, 3H). $^{13}$C NMR (125 MHz, DMSO-d$_6$): δ168.8, 148.9, 148.1, 147.4, 140.2, 136.1, 130.5, 129.6, 128.1, 125.4, 125.3, 124.7, 124.6, 123.6, 122.8, 120.5, 120.1, 119.9, 119.6, 118.5, 116.0, 114.8, 113.9, 112.1, 111.9, 108.9, 94.7, 82.0, 74.9, 55.5, 55.5, 49.5, 45.5, 29.6, 28.6. IR (thin film/NaCl): 3324.0 (brm), 2995.0 (w), 2911.3 (m), 1660.0 (s), 1589.7 (m), 1513.5 (s), 1461.1 (s), 1417.9 (m), 1399.0 (m), 1349.2 (s), 1315.5 (m), 1260.0 (s), 1234.6 (m), 1124.4 (m), 1027.2 (m), 741.7 (s) cm$^{-1}$. [αD$^{20}$−18° (c=0.1, CH$_2$Cl$_2$).

Preparation of methoxy oxime (−)-57 To a mixture of oxime (−)-56 (90 mg, 0.15 mmol), MeI (88 μL, 1.42 mmol), and powdered KOH (88 mg, 1.58 mmol) was added n-Bu$_4$NBr (10 mg, 0.03 mmol). The mixture was stirred under N$_2$ for 30 min, solvent was removed in vacuo, and the residue was subjected to silica gel chromatography (1:1 hexanes:ethyl acetate) to provide methoxime (−)-57 (85 mg, 90%) as a yellow powder. $^1$H NMR (500 MHz, DMSO-d$_6$, 345 K): δ93.6 (d, J=8.0 Hz, 1H), 7.99 (d, J=8.6 Hz, 1H), 7.93 (d, J=7.8 Hz, 1H), 7.68 (d, J=8.3 Hz, 1H), 7.51 (app.t, J=7.6 Hz, 1H), 7.44 (app.t, J=7.8 Hz, 1H), 7.33 (app.t, J=7.2 Hz, 1H), 7.30 (app.t, J=7.1 Hz, 1H), 7.04 (s, 1H), 7.02 (d, J=5.6 Hz, 1H), 6.97 (d, J=9.4 Hz, 1H), 6.94 (d, J=8.1 Hz, 1H), 4.97 (s, 2H), 4.86 (d, J=15.5 Hz, 1H), 4.85 (d, J=15.7 Hz, 1H), 4.76 (s, 1H), 3.76 (s, 3H), 3.74 (s, 3H), 3.54 (d, J=14.4 Hz, 1H), 3.45 (s, 3H), 3.16 (dd, J=5.9, 14.4 Hz, 1H), 3.14 (s, 3H), 2.46 (s, 3H). $^{13}$C NMR (125 MHz, DMSO-d$_6$): δ168.7, 148.9, 148.1, 147.3, 139.8, 136.1, 130.4, 129.5, 128.0, 125.4, 125.3, 124.7, 124.6, 123.6, 122.7, 120.6, 120.2, 119.9, 119.6, 118.6, 115.5, 114.9, 113.8, 112.2, 112.0, 108.9, 96.1, 83.3, 82.0, 60.8, 58.4, 55.5, 55.5, 49.5, 45.4, 30.4, 28.5. IR (thin film/NaCl): 2998.0 (w), 2926.3 (m), 1674.1 (s), 1590.0 (m), 1513.7 (s), 1460.9 (m), 1418.2 (m), 1397.9 (s), 1349.4 (s), 1316.2 (s), 1262.1 (m), 1225.6 (m), 1044.3 (m), 743.5 (m) cm$^{-1}$. [α]D$^{25}$−22° (c=0.1, CH$_2$Cl$_2$).

Preparation of amine (+)-58 A mixture of oxime (+)-5 (85 mg, 0.13 mmol) and PtO$_2$(28 mg) in a 60% aqueous acetic acid (15.0 mL) was treated with H$_2$, and the reaction was monitored by TLC (1:1 hexanes:ethyl acetate). Upon completion, the mixture was filtered through celite and the filtrate was evaporated. The residue was dissolved in CH$_2$Cl$_2$ (40 mL) and washed with 8.0 mL 1.0N NaOH. The aqueous layer was then back-extracted with CH$_2$Cl$_2$ (2×15 mL). The combined organic layers were dried over Na$_2$SO$_4$ and evaporated to a residue (79 mg), which was used in the next step without further purification. An analitical sample of primary amine (+)-58 could be obtained by preparative TLC of the above residue using 5% MeOH:CH$_2$Cl$_2$ as eluent. $^1$H NMR (500 MHz, CDCl$_3$, 310 K): δ9.55 (d, J=7.9 Hz, 1H), 7.95 (d, J=8.5 Hz, 1H), 7.88 (d, J=7.7 Hz, 1H), 7.51 (app.t, J=7.6 Hz, 1H), 7.42 (app.t, J=8.2 Hz, 1H), 7.40 (app.t, J=7.5 Hz, 1H), 7.30 (app.t, J=7.8 Hz, 2H), 6.99 (d, J=9.4 Hz, 2H), 6.87 (d, J=8.0 Hz, 1H), 6.59 (d, J=4.9 Hz, 1H), 4.98 (d, J=14.9 Hz, 1H), 4.92 (d, J=14.9 Hz, 1H), 4.87 (d, J=16.7 Hz, 1H), 4.82 (d, J=16.7 Hz, 1H), 3.88 (s, 3H), 3.86 (s, 3H), 3.75 (m, 2H), 3.46 (s, 3H), 2.63 (m, 2H), 2.32 (s, 3H), 1.27 (bs, 2H), $^{13}$C NMR (125 MHz, CDCl$_3$, 315 K): δ170.2, 149.6, 148.7, 140.1, 137.0, 130.8, 129.6, 129.5, 127.0, 126.2, 125.4, 124.7, 124.5, 123.8, 120.8, 120.5, 120.2, 120.2, 119.6, 116.0, 115.4, 114.6, 111.6, 111.6, 107.4, 91.3, 84.2, 80.2, 57.5, 56.1, 56.1, 49.9, 46.5, 42.6, 34.6, 30.0. IR (thin film/NaCl): 3414.7 (brw), 2920.8 (s), 2851.7 (s), 1733.7 (w), 1672.8 (s), 1636.0 (w), 1588.1 (m), 1513.5 (s), 1352.7 (s), 1259.3 (s), 1136.7 (m), 744.2 (m) cm$^{-1}$. [α]D$^{25}$+14.3° (c=0.14, CHCl$_3$).

Preparation of (+)-staurosporine (49) Crude amine (+)-58 was dissolved in THF (2.0 mL) and treated with formic acetic anhydride in THF (1.3 μL of a 1.3 M solution in THF, 0.17 mmol)(FAA prepared by treatment of 1.0 equiv acetic anydride with 1.2 equiv formic acid followed by reflux for 2 h). TLC analysis showed rapid formation of a less polar substance. A stream of N$_2$ was used to evaporate the solvent, followed by high vacuum for 15 min. THF (1.3 mL) was added to dissolve the residue, the reaction vessel was cooled to 0° C., and BH$_3$·DMS(193 μL of a 2.0 N solution in toluene, 0.39 mmol) was introduced. The solution was heated to reflux for 2 h at which point it was again cooled to 0° C. Methanolic HCl (1.0 mL) was added along with excess MeOH (1.3 mL) and the solution was refluxed for an additional hour. Following cooling, volitiles were removed in vacuo, and the solid residue was azetroped with MeOH (5×5.0 mL). To the remaining residue was added 7.0 mL CH$_2$Cl$_2$ followed by 1.0 N NaOH (5.0 mL), layers were separated, and the aqueous layer was extracted with CH$_2$Cl$_2$ (3×7.0 mL). Combined organic layers were dried over Na$_2$SO$_4$, evaporated, and purified by MPLC (5% MeOH: CH$_2$Cl$_2$) to give a methyl amine (80 mg, 91% 2 steps from 14) as a yellow foam. $^1$H NMR (500 MHz, CDCl$_3$, 320° K): δ9.55 (d, J=7.9 Hz, 1H), 7.89 (d, J=8.5 Hz, 1H), 7.82 (d, J=7.3 Hz, 1H), 7.48 (td, J=1.0, 7.5 Hz, 1H), 7.39 (td, J=1.0, 7.4 Hz, 1H), 7.38 (app.t, J=7.3 Hz, 1H), 7.27 (m, 2H), 7.01 (m, 2H), 6.88 (d, J=8.7 Hz, 1H), 6.57 (dd, J=1.4, 6.0 Hz, 1H), 4.98 (d, J=14.9 Hz, 1H), 4.91 (d, J=14.9 Hz, 1H), 4.84 (s, 2H), 3.92 (d, J=3.0 Hz, 1H), 3.88 (s, 3H), 3.87 (s, 3H), 3.37 (dd, J=3.8, 7.7 Hz, 1H), 3.33 (bs, 3H), 2.72 (ddd, J=1.3, 4.6, 14.5 Hz, 1H), 2.46 (m, 1H), 2.35 (s, 3H). $^{13}$C NMR (125 MHz, CDCl$_3$): δ170.4, 149.3, 148.4, 139.6, 136.7, 130.6, 130.4, 129.3, 127.1, 126.6, 125.1, 124.5, 124.3, 123.5, 120.7, 120.4, 120.0, 119.8, 119.1, 115.5, 114.9, 114.0, 111.2, 111.2, 107.0, 91.2, 83.9, 80.2, 57.5, 56.0, 55.9, 50.7, 49.9, 46.4, 33.2, 30.1, 29.9. IR (thin film/NaCl): 2954.1 (m), 2915.1 (m), 1673.2 (s), 1635.8 (m), 1462.7 (s), 1399.0 (s), 1352.6 (s), 1258.7 (m), 1136.5 (m), 1026.9 (m), 745.2 (s) cm$^{-1}$. $[\alpha]D^{25}$+22° (c=0.1, MeOH). To a stirred solution of the amine (10 mg, 0.016 mmol) in anisole or thioanisole (80 μL, =50 equiv) was added TFA (0.5 mL). The sluggish reaction was monitored by TLC, and after 48 h had proceeded to completion, whereupon 1.0 mL H$_2$O was added, and the solution was adjusted to pH10 with 5.0 N NaOH, followed by extraction with CH$_2$Cl$_2$ (3×5 mL). Combined organic layers were dried over Na$_2$SO$_4$, and evaporated to a residue, which was purified by preparative TLC (5% MeOH: CH$_2$Cl$_2$) to provide (+)-Staurosporine (49, 6 mg, 70%). $^1$H NMR (500 MHz, CDCl$_3$): δ 9.43 (d, J=7.9 Hz, 1H), 7.94 (8.5, 1H), 7.90 (d, J=7.7 Hz, 1H), 7.49 (app.t, J=7.6 Hz, 1H), 7.43 (app.t, J=7.7 Hz, 1H), 7.37 (app.t, J=7.5 Hz, 1H), 7.33 (app.t, J=7.4 Hz, 1H), 7.30 (d, J=8.0 Hz, 1H), 6.57 (d, J=5.6 Hz, 1H), 6.33 (bs, 1H), 5.05 (d, J=15.8 Hz, 1H), 5.01 (d, J=15.8 Hz, 1H), 3.89 (bs, 1H), 3.42 (s, 3H), 3.37 (d, 3.2H), 2.76 (dd, J=3.9, 14.7 Hz, 1H), 2.41 (bd, J=15.4 Hz, 1H), 2.37 (s, 3H), 1.59 (bs, 1H), 1.57 (s, 3H). $^{13}$C NMR (125 MHz, CDCl$_3$): δ173.6, 139.8, 136.7, 132.2, 130.8, 126.6, 125.0, 124.6, 124.2, 123.4, 120.6, 120.0, 119.8, 115.3, 114.1, 106.9, 91.1, 84.2, 80.1, 57.2, 50.4, 45.9, 33.3. 30.3, 30.1. IR (thin film/NaCl): 3316.6 (m), 2925.0 (m), 2850.8 (m), 1678.7 (s), 1636.2 (m), 1584.2 (m), 1457.5 (s), 1852.2 (s), 1316.7 (s), 1281.3 (m), 115.5 (m), 744.8 (s) cm$^{-1}$. $[\alpha]D^{25}$+35° (c=0.1MeOH): natural staurosporine $[\alpha]D^{25}$+35° (c=1.0, MeOH).

In summary, efforts to devise an efficient synthesis of the pyranosylated indolocarbazoles via a common intermediate [i.e., (+)-36] were successful in delivering (+)-49 (19 steps), (+)-50 (17 steps), and (+)-51 (19 steps). In addition, these investigations have revealed both ring-expansion and -contraction reactivity that may play a central role in the biogenesis of both the furanosylated and pyranosylated members of this important class of natural products.

Experimental procedures for selected compounds in Examples 1 to 4 may be found in international publication number WO 97/07081 to Yale University and Wood, et a., 27 Feb. 1997, filed as PCT/IB96/00987 on 9 Aug. 1996, claiming priority benefit of U.S. application Ser. No. 60/002,164 filed 11 Aug. 1995, which is incoporated by reference.

REFERENCES

Fredenhagen, A.; Peter, H. H. *Tetrahedron* 52:1235 (1996).

Link, J. T., et al., *J. Am. Chem. Soc.* 115:3782 (1993).

Ootsuka, Y. et al., Jpn. Kokai Tokkyo Koho JP05247054, (1993).

Omura, S. et al., *J. Antibiotics* 48:525 (1995).

McCombie, S. W., et al., *Bioorg. Med. Chem. Lett.* 3:1537 (1993).

Pirrung, M. C., et al., *J. Org. Chem.* 60:2112 (1995).

Stolz, B. M., and Wood, J. L., *Tetrahedron Lett.* 36:8543–8544 (1995).

Stoltz, B. M., and Wood, J. L., *Tetrahedron Lett.* 37:3929–3930 (1996).

Wood, J. L., et al., *J. Amer. Chem. Soc.* 117:10413–10414 (1995).

Wood, J. L., et al., *J. Amer. Chem. Soc.* 118:10656–10657 (1996).

Wood, J. L., et al., *Tetrahedron Lett.* 37:7335–7336 (1996).

All the references cited herein are expressly incorporated herein by reference. The invention was made with partial government support under American Cancer Society grant JFRA-523. The government has certain rights in the invention.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The invention claimed is:

1. A process for the preparation of furanosylated indolocarbazoles by reacting an indolocarbazole having the ring structure

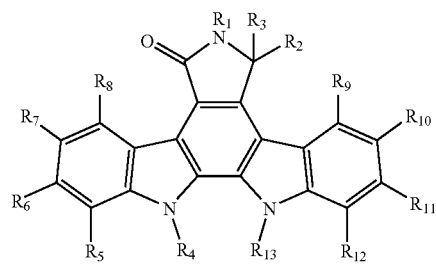

with an acetal having the structure

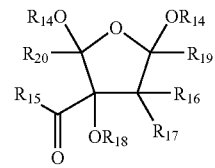

under the conditions that promote acetal exchange or formation to produce a furanosylated product having the ring structure

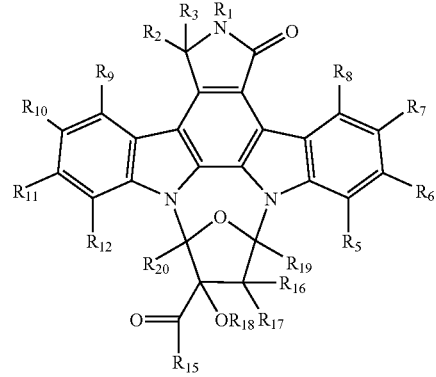

wherein:
R₁ is selected from the group consisting of 3,4-DMB, PMB, Bn, and t-Bu;
R₂–R₄, R₆–R₁₃, and R₁₆–R₁₉ are hydrogen;
R₅ is hydrogen;
R₁₄ and R₂₀ are CH₃, and
R₁₀ is OCH₃.

2. A process according to claim 1 wherein the acetal is a furanose of the formula

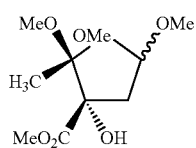

and is reacted with DMB-protected K252c to give two products of the formulae

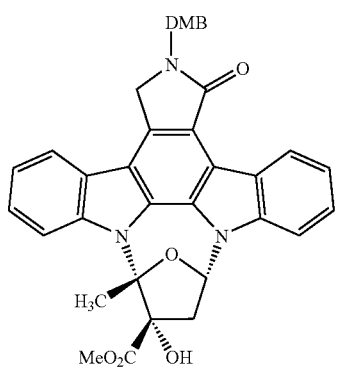

and

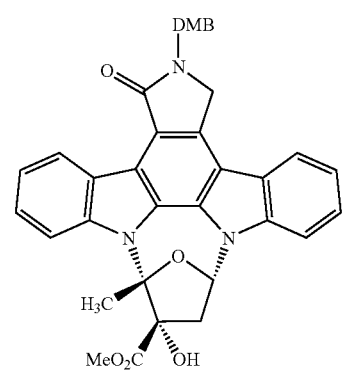

3. A product prepared according to the process of claim 1.

4. A process according to claim 1 wherein the indolocarbazole is prepared by reacting a diazo compound having the ring structure

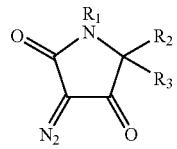

with a biindole having the ring structure

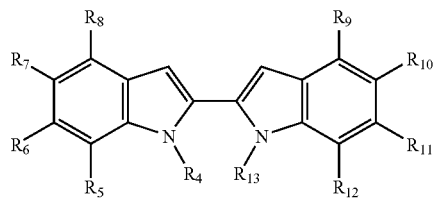

5. A process according to claim 4 wherein the reaction is carried out in the presence of a transition metal catalyst in a solvent capable of solvating the reactants.

6. A process according to claim 4 wherein the coupling reaction is carried out in the presence of a Rh₂(OAc)₄ catalyst.

7. A process according to claim 4 wherein the diazo compound is a diazolactam and the biindole is a 2,2'-biindole.

8. A process according to claim 1 wherein the indolocarbazole is reacted with an acetal under conditions that promote acetal exchange.

9. A process according to claim 1 wherein said preparation is carried out in the presence of a Bronsted acid or a Lewis acid.

10. A process for the preparation of furanosylated indolocarbazoles comprising:
reacting a diazo compound having the ring structure

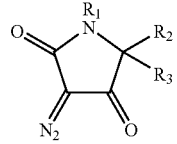

with a biindole having the ring structure

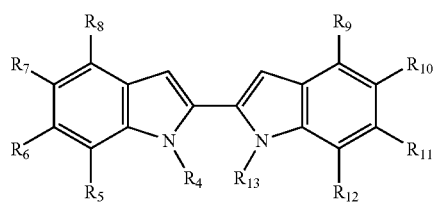

in the presence of a transition metal catalysts in a solvent capable of solvating the reactants, to produce an indolocarbazole having the ring structure

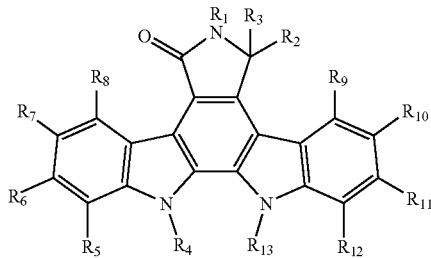

and then reacting the indolocarbazole with an acetal having the structure

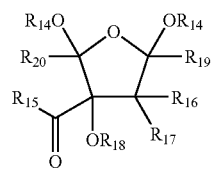

to produce a furanosylated product having the ring structure

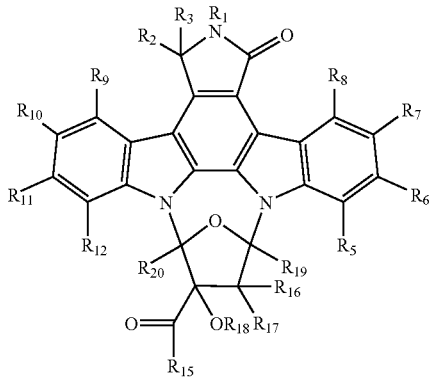

wherein:
$R_1$ is selected from the group consisting of 3,4-DMB, PMB, Bn, and t-Bu;
$R_2$–$R_4$, $R_6$–$R_{13}$, and $R_{16}$–$R_{19}$ are hydrogen;
$R_5$ is hydrogen;
$R_{14}$ and $R_{20}$ are $CH_3$, and
$R_{15}$ is $OCH_3$.

11. A process according to claim 10 wherein the furanosylated indolocarbazole prepared is K252a.

12. A product produced by the process of claim 10.

13. A process according to claim 10 wherein the biindole is a 2,2'-biindole.

14. A process according to claim 10 wherein a Lewis acid is employed.

* * * * *